(12) United States Patent
Hoffmann et al.

(10) Patent No.: US 7,446,090 B2
(45) Date of Patent: Nov. 4, 2008

(54) FSH FORMULATION

(75) Inventors: James Arthur Hoffmann, Greenwood, IN (US); Jirong Lu, Indianapolis, IN (US)

(73) Assignee: Ares Trading S.A., Aubonne (CH)

( * ) Notice: Subject to any disclaimer, the term of this patent is extended or adjusted under 35 U.S.C. 154(b) by 39 days.

(21) Appl. No.: 11/482,569

(22) Filed: Jul. 7, 2006

(65) Prior Publication Data

US 2006/0241047 A1 Oct. 26, 2006

Related U.S. Application Data

(60) Continuation of application No. 09/928,198, filed on Aug. 10, 2001, now abandoned, which is a division of application No. 09/744,431, filed as application No. PCT/US99/16031 on Jul. 15, 1999, now abandoned.

(60) Provisional application No. 60/100,696, filed on Sep. 17, 1998, provisional application No. 60/098,711, filed on Sep. 1, 1998, provisional application No. 60/094,767, filed on Jul. 31, 1998, provisional application No. 60/094,611, filed on Jul. 30, 1998, provisional application No. 60/093,906, filed on Jul. 23, 1998.

(51) Int. Cl.
*A61K 38/24* (2006.01)
*C07K 14/59* (2006.01)

(52) U.S. Cl. .............................. 514/2; 530/399; 530/398

(58) Field of Classification Search ........................ None
See application file for complete search history.

(56) References Cited

U.S. PATENT DOCUMENTS

| | | | |
|---|---|---|---|
| 4,496,537 A | 1/1985 | Kwan | |
| 4,589,402 A | 5/1986 | Hodgen et al. | |
| 4,659,696 A | 4/1987 | Hirai et al. | |
| 4,670,419 A | 6/1987 | Uda et al. | |
| 4,746,508 A | 5/1988 | Carey et al. | |
| 4,758,552 A * | 7/1988 | Gulyas et al. | 514/15 |
| 4,847,079 A | 7/1989 | Kwan | |
| 4,962,091 A | 10/1990 | Eppstein et al. | |
| 5,087,615 A | 2/1992 | Chappel et al. | |
| 5,128,453 A | 7/1992 | Arpaia et al. | |
| 5,162,306 A | 11/1992 | Donaldson | |
| 5,270,057 A | 12/1993 | de Meere et al. | |
| 5,356,876 A | 10/1994 | Espey | |
| 5,374,620 A | 12/1994 | Clark et al. | |
| 5,384,132 A | 1/1995 | De Meere et al. | |
| 5,508,261 A * | 4/1996 | Moyle et al. | 514/8 |
| 5,580,856 A | 12/1996 | Prestrelski et al. | |
| 5,639,640 A | 6/1997 | Reddy et al. | |
| 5,650,390 A | 7/1997 | Samaritani et al. | |
| 5,661,125 A | 8/1997 | Strickland | |
| 5,681,822 A | 10/1997 | Bornstein et al. | |
| 5,733,572 A | 3/1998 | Unger et al. | |
| 5,767,067 A | 6/1998 | Arpaia et al. | |
| 5,811,096 A | 9/1998 | Aleman et al. | |
| 5,889,110 A | 3/1999 | Hutchinson et al. | |
| 5,929,028 A | 7/1999 | Skrabanja et al. | |
| 5,945,187 A | 8/1999 | Buch-Rasmussen et al. | |
| 6,066,620 A | 5/2000 | McGregor et al. | |
| 6,136,784 A | 10/2000 | L'Italien et al. | |
| 6,238,890 B1 | 5/2001 | Boime et al. | |
| 6,267,958 B1 | 7/2001 | Andya et al. | |
| 6,440,930 B1 | 8/2002 | Rinella, Jr. | |
| 6,541,606 B2 | 4/2003 | Margolin et al. | |
| 6,573,237 B2 | 6/2003 | Rinella, Jr. | |
| 2003/0072803 A1 | 4/2003 | Goldenberg et al. | |

FOREIGN PATENT DOCUMENTS

| | | |
|---|---|---|
| CA | 1340132 | 11/1998 |
| DE | 41 17 078 A1 | 11/1882 |
| EP | 0 318 081 | 5/1989 |
| EP | 0 448 146 | 9/1991 |
| EP | 0 652 766 | 7/1993 |
| EP | 0 603 159 | 6/1994 |
| EP | 0 853 945 | 7/1998 |
| EP | 0 920 873 | 12/1998 |
| EP | 0 891 774 | 1/1999 |
| EP | 0 668 073 | 4/1999 |

(Continued)

OTHER PUBLICATIONS

Pimpalkhute et al. RAdioimmunoassay of Human FSH. Journal of Radioanalytical and Nuclear Chemistry. Abstract. vol. 103, No. 2, pp. 105-116; (1986).*

Akers Michael J., "Considerations in selecting antimicrobial preservative agents for parenteral product development", Pharmaceutical Technology, May 1984, pp. 36-46.

Akers, Michael J., "Excipient—Drug Interactions in Parenteral Formulations", Journal of Pharmaceutical Sciences, Nov. 2002, vol. 91, No. 11, pp. 2283-2300.

Amir, Syed M. et al., "Phenol, A Potent Stimulator of Adenylate Cyclase in Human Thyroid Membranes", Endocrine Research Communications, 8(2):83-95, 1981.

Package insert for A.P.L. (Wyeth Laboratories) dated Dec. 4, 1974.

Approved Drug and Legal Requirements, 20th Edition, 2000.

Arzneiformenlehre, Paul Heinz List, Wissenschaftliche Verlagsgellschaft mbH, Stuttgart, 4th Edition, 1985, pp. 402-407.

(Continued)

*Primary Examiner*—Marianne P Allen
*Assistant Examiner*—Regina M DeBerry
(74) *Attorney, Agent, or Firm*—Woodard, Emhardt, Moriarty, McNett & Henry LLP

(57) ABSTRACT

This invention relates to FSH or a FSH variant containing an alpha and beta subunit contained in formulations, and articles of manufacture. The invention provides advantageous new proteins and nucleic acids, multi-use pharmaceutical solutions, formulations and products of said proteins and nucleic acids where none approved for commercial use had previously existed having such extended use indications. These products are particularly useful in therapeutic regimens for increasing serum levels of FSH or a FSH variant over a period of treatment. Thus, inter alia, the invention fills the need for convenient products of FSH or from a FSH variant.

32 Claims, No Drawings

FOREIGN PATENT DOCUMENTS

| | | |
|---|---|---|
| EP | 1 191 099 | 6/1999 |
| EP | 0 736 303 | 8/1999 |
| EP | 0 974 359 | 1/2000 |
| FR | 2782455 | 2/2000 |
| GB | 839 300 | 8/1958 |
| GB | 1065127 | 4/1967 |
| WO | WO 92/21332 | 12/1992 |
| WO | WO 92/22568 | 12/1992 |
| WO | WO 93/11788 | 6/1993 |
| WO | WO 94/03198 | 2/1994 |
| WO | WO 97/04801 | 2/1997 |
| WO | WO 97/17087 | 5/1997 |
| WO | WO 98/30592 | 7/1998 |
| WO | WO 99/21534 | 5/1999 |

OTHER PUBLICATIONS

Baenziger, Jacques U. et al., "Pituitary Glycoprotein Hormone Oligosaccharides: Structure, Synthesis and Function of the Asparagine-Linked Oligosaccharides on Lutropin, Follitropin, and Thyrotropin", Biochimica et Biophysica Acta, 1988, 947:287-306.

Boime, Irving et al., "Glycoprotein Hormone Structure-Function and Analog Design", Recent Progress in Hormone Research, vol. 54, 1999, The Endocrine Society, pp. 271-289.

Burgues et al., "Subcutaneous self-administration of highly purified follicle stimulating hormone and human chorionic gonadotrophin for the treatment of male hypogonadotropic hypogonadism", Human Reproduction, 1997, vol. 12, No. 5, pp. 980-986.

Combarnous, Yves, "Molecular Basis of the Specificity of Binding of Glycoprotein Hormones to Their Receptors", Endocrine Reviews, 1992, vol. 13, No. 4, pp. 670-691.

CPMP Guidelines antimicrobial preservation inclusion, CPMP/CVMP/OWP/115/95, Jul. 8, 1997, pp. 1-6.

de Medeiros, S.F. et al., "Stability of Immunoreactive β-Core Fragment of hCG", Obstetrics & Gynecology, vol. 77, No. 1, Jan. 1991, pp. 53-59.

European Agency for the Evaluation of Medicinal Products, Committee for Proprietary Medicinal Products (CPMP), "Note for Guidance on Maximum Shelf-life for Sterile Products for Human Use After First Opening or Following Reconstitution", Guidance CPMP/QWP/159/96, 1999.

European Pharmacopia, 1997 (last revised version of 2001), pp. 1-6.

Extract from Handbook of Pharmaceutical Excipients, 3rd Edition, 2000, pp. 41-43.

Fiddes et al., "Structure, Expression, and Evolution of the Genes for the Human Glycoprotein Hormones", Recent Progress in Hormone Research, 1984, vol. 40, pp. 43-78.

Fiddes et al., "The Gene Encoding the Common Alpha Subunit of the Four Human Glycoprotein Hormones", Journal of Molecular and Applied Genetics, 1981, vol. 1, pp. 3-18.

Fransson, Jonas et al., "Solvent Effects on the Solubility and Physical Stability of Human Insulin-Like Growth Factor 1", Pharmaceutical Research 14(5):606-12, 1997.

Frenken, L.A.M. et al., "Analysis of the Efficacy of Measures to Reduce Pain After Subcutaneous Administration of Epoetin Alfa", Nephrology Dialysis Transplantation 9:1295-98, 1994.

Furuhashi, M. et al. "Fusing the Carboxy-Terminal Peptide of the Chorionic Gonadotropin (CG) beta Subunit to the Common alpha-Subunit: Retention of O-linked Glycosylation and Enhanced in Vivo Bioactivity of Chimeric Human CG", Molecular Endocrinology, 1995, vol. 9, No. 1, pp. 54-63.

Garcia-Campayo, Vincenta et al., "Design of Stable Biologically Active Recombinant Lutropin Analogs", Nature Biotechnology 15:663-67, 1997.

Gennaro et al., Remington's Pharmaceutical Sciences (18th Edition, Mack Publishing. Co., 1990, see part 8 "Pharmaceutical Preparations and their Manufacture," pp. 1545-1569.

Gonal-F® (follitropin alfa for injection) For subcutaneous injection: Package Insert Code N1900101B, manufactured by Serono Laboratories, Inc., Randolph, MA, USA, published Sep. 1997.

Guzman et al., "The Gene Encoding Ovine Follicle-Stimulating Hormone beta: Isolation, Characterization, and Comparison to a Related Ovine Genomic Sequence", DNA and Cell Biology, 1991, vol. 10, No. 8, pp. 593-601.

Harvey, Stewart C., "Antiseptics and Disinfectants; Fungicides; Ectoparasiticides", The Pharmacological Basis of Therapeutics, 6th Edition, Chapter 41, 964-987, 1980.

Heikoop, Judith C. et al., "Structure-based design and protein engineering of intersubunit disulfide bonds in gonadotropins" Nature Biotechnology, Jul. 1997, vol. 15, pp. 658-662.

Hirai, T. et al., "The gene for the β subunit of porcine FSH: absence of consensus oestrogen-responsive element and presence of retroposons", Journal of Molecular Endocrinology, 1990, vol. 5, pp. 147-158.

J. Parental Drug Assoc. Nov.-Dec. 1980, vol. 34, No. 6.

Jorgenson, Jan Trost, "Improvement of Patient Convenience in Treatment with Growth Hormone", Journal of Pediatric Endocrinology, 1994, 7(2):175-180.

Keene et al., Expression of Biologically Active Human Follitropin in Chinese Hamster Ovary Cells. The Journal of Biological Chemistry vol. 264/9: 4769-4775.

Kesner, J.S. et al., "Stability of Urinary Female Reproductive Hormones Stored Under Various Conditions", Reproductive Toxicology, vol. 9, No. 3, pp. 239-244, 1995.

Keutmann, Henry T. et al., "Structure of Human Luteinizing Hormone Beta Subunit: Evidence for a Related Carboxyl-Terminal Sequence Among Certain Peptide Hormones", Biochemical and Biophysical Research Communications, 1979, vol. 90, No. 3., pp. 842-848.

Klein et al., "Pharmacokinetics and pharmacodynamics of single-chain recombinant human follicle-stimulating hormone containing the human chorionic gonadotropin carboxyterminal peptide in the rhesus monkey", Fertility and Sterility, 2002, vol. 77, No. 6, pp. 1248-1255.

Kumar et al., "Cloning of the mouse gonadotropin beta-subunit-encoding genes, II. Structure of the luteinizing hormone beta-subunit-encoding genes", Gene, 1995, vol. 166, pp. 335-336.

Kumar et al., "Cloning of the mouse gonadotropin beta-subunit-encoding genes, I. Structure of the follicle-stimulating hormone beat-subunit-encoding gene", Gene, 1995, vol. 166, pp. 333-334.

Lam, Xanthe M. et al., "The Effect of Benzyl Alcohol on Recombinant Human Interferon-γ" Pharmaceutical Research, 1997, vol. 14, No. 6, 725-729.

Livesey J. H. et al., "Glycerol prevents loss of immunoreactive follicle-stimulating hormone and luteinizing hormone from frozen urine", Journal of Endocrinology, vol. 98, pp. 381-384, 1983.

Livesey, J. H. et al., "Effect of Time, Temperature and Freezing on the Stability of Immunoreative LH, FSH, TSH, Growth Hormone, Prolactin and Insulin in Plasma", The Medical Unit, Princess Margaret Hospital, Christchurch 2, New Zealand, Jun. 25, 1980, Biochem 13 (4), 1980, pp. 151-155.

Maa, Yuh-Fun, et al., "Aggregation of recombinant human growth hormone induced by phenolic compounds", International Journal of Pharmaceutics, 1996, vol. 140, pp. 155-168.

Maurer et al., "Molecular Cloning and Nucleotide Sequence Analysis of Complementary Deoxyribonucleic Acid for the beta-Subunit of Rat Follicle Stimulating Hormone", Molecular Endocrinoloy, 1987, vol. 1, pp. 717-723.

Maurer et al., "Isolation and Nucleotide Sequence Analysis of a Cloned cDNA Encoding the β-Subunit of Bovine Follicle-Stimulating Hormone", DNA, vol. 5, No. 5, pp. 363-369, 1986.

Newman et al. "Use of Nonionic Block Copolymers in Vaccines and Therapeutics", Critical Reviews in Therapeutic Drug Carrier Systems, 1998, vol. 15, No. 2, pp. 89-140.

Pierce, John G. & Parsons, Thomas F., "Glycoprotein Hormones: Structure and Function", Ann. Rev. Biochem. 50:465-95, 1981.

Pimpalkhute, M. et al., "Radioimmunoassay of Human Follicle Stimulating Hormone/HFSH/", J. Radioanal. Nucl. Chem. Letters, 1986, 103, No. 2, pp. 105-116.

"Pregnyl Prescribing Information," Organon Inc., Aug. 1998.

Rafferty, M.J. et al., "Safety and Tolerability of a Multidose Formulation of Epoetin Beta in Dialysis Patients", Clinical Nephrology. 54(3):240-45, 2000.

Reichert, Leo E. et al., "Dissociation of Human Follicle-stimulating Hormone", The Journal of Biological Chemistry, 1975, vol. 250, No. 8, pp. 3034-3040.

Remmele Jr., Richard L. et al., "Interleukin-1 Receptor (IL-1R) Liquid Formulation Development Using Differential Scanning Calorimetry", Pharmaceutical Research, 1998, vol. 15, No. 2, pp. 200-208.

Rose, M.P. et al, "Characterisation, calibration and comparison by international collaborative study of international standards for the calibration of therapeutic preparations of FSH", Journal of Endocrinology, vol. 158, pp. 97-114, 1998.

St. Peter, Wendy L. et al., "Pain Comparison After Subcutaneous Administration of Single-Dose Formulation Versus Multidose Formulation of Epogen in Hemodialysis Patients", American Journal of Kidney Diseases, 32(3):470-74, 1998.

Saketos, Maria et al., "Time-Resolved Immunofluorometric Assay and Specimen Storage Conditions for Measuring Urinary Gonadotropins", Clinical Chemistry, vol. 40, No. 5, 1974, pp. 749-753.

Saxena, B.B. et al., "Amino Acid Sequence of the β Subunit of Follicle-stimulating Hormone from Human Pituitary Glands", The Journal of Biological Chemistry, vol. 251, No. 4, pp. 993-1005, Feb. 25, 1976.

Serono Study Report GF 9873, "Evaluation of FSH Formulations claimed in EP-974'359", dated Mar. 22, 2004.

Shome, B. et al., "A Reevaluation of the Amino Acid Sequence of Human Follitropin beta-Subunit", Journal of Protein Chemistry, 1988, vol. 7., No. 4, pp. 325-339.

Shome, B. et al., "Human Follicle Stimulating Hormone: First Proposal for the Amino Acid Sequence of the Hormone-Specific, β Subunit (hFSHβ)", J. Clin. Endocrinol. Metab., vol. 39, 187, pp. 203-205, 1974.

Steelman et al., "Assay of the Follicle Stimulating Hormone Based on the Augmentation with Human Chorionic Gonadotropin", Endocrinology, 1953, vol. 53, pp. 604-616.

Strickland, Thomas W. et al, "The Kinetic and Equilibrium Parameters of Subunit Association and Gonadotropin Dissociation", The Journal of Biological Chemistry, 1982, vol. 257, No. 6 pp. 2954-2960.

Sugahara, Tadashi et al., "Expression of biologically active fusion genes encoding the common α subunit and either the CGβ or FSHβ subunits: role of a linker sequence", Molecular and Cellular Endocrinology 125 (1996) pp. 71-77.

Talmadge et al., "Evolution of the genes for the beta subunits of human chorionic gonadotropin and luteinizing hormone", Nature, 1984, vol. 307, pp. 37-40.

Tobler, S.A. et al., "Benzyl Alcohol-Induced Destabilization of Interferon-γ: A Study by Hydrogen-Deuterium Isotope Exchange", Journal of Pharmaceutical Sciences, vol. 93, No. 6, Jun. 2004.

"The United States Pharmacopeia, Twenty-First Revision", United States Pharmacopeial Convention, Inc., Official from Jan. 1, 1985, prepared by the Committee of Revision and published by the Board of Trustees, pp. 1491-1493, 1984.

Vahl, et al., "Bioavailability of Recombinant Human Growth Hormone in Different Concentrations and Formulations", Pharmacology & Toxicology 79:144-49, 1996.

Van Hell et al., "Effects of Human Menopausal Gonadotrophin Preparations in Different Bioassay Methods", Acta Endocrinologica, 1964, vol. 47, pp. 409-418.

Voortman, Gerritt et al, "Bioequivalence of subcutaneous injections of recombinant human follicle stimulating hormone (Puregon®) by Pen-injector and syringe", Human Reproduction, 1999, vol. 14, No. 7, pp. 1698-1702.

Wallhausser K-H, "Antimicrobial Preservatives in Europe: Experience with Preservatives Used in Pharmaceuticals and Cosmetics", International Symposium on Preservation in Biological Products, San Francisco 1973, Develop. Biol. Standard, vol. 24, pp. 9-28, 1974.

Watkins et al., "DNA Sequence and Regional Assignment of the Human Follicle-Stimulating Hormone beta-Subunit Gene to the Short Arm of Human Chromosome 11", DNA, 1987, vol. 6, No. 3, pp. 205-212.

Wenzel et al. "Pluronic F127 gel formulations of Deslorelin and GnRH reduce drug degradation and sustain drug release and effect in cattle", Journal of Controlled Release, 2002, vol. 85, pp. 51-59.

Anchordoquy, Thomas J. et al., "Polymers Protect Lactate Dehydrogenase during Freeze-Drying by Inhibiting Dissociation in the Frozen State", Archives of Biochemistry and Biophysics, vol. 332, No. 2, Aug. 15, 1996, Article No. 0337, pp. 231-238.

Anik, Shabbir T. et al., "Adsorption of D-Nal(2) $^6$LHRH, a decapeptide, onto glass and other surfaces", Insitute of Pharmaceutical Sciences, Syntax Research, Palo Alto, CA, International Journal of Pharmaceutics, vol. 16, 1983, pp. 181-190.

Bam, Narendra B. et al. "Stability of Protein Formulations: Investigation of Surfactant Effects by a Novel EPR Spectroscopic Technique", Research Article, Pharmaceutical Research, vol. 12, No. 1, 1995, pp. 2-11.

Baselga, Jose et al., "Phase II Study of Weekly Intravenous Recombinant Humanized Anti-p185$^{HER2}$ Monoclonal Antibody in Patients with HER2/*neu*-Overexpressing Metastic Breast Cancer", Journal of Clinical Oncology, vol. 14, No. 3, Mar. 1996, pp. 737-744.

Boulet, Louis-Philippe et al., "Inhibitory Effects of an Anti-IgE Antibody E25 on Allergen-induced Early Asthmatic Response", Am J Respir Crit Care Med., vol. 155, 1997, pp. 1835-1840.

Butt, W. R., "The Iodination of Follicle-Stimulating and Other Hormones for Radioimmunoassay", J. Endocr., 1972, vol. 55, pp. 453-454.

Jentoft, Neil, "Why are proteins O-glycosylated?", TIBS 15, Aug. 1990, Elsevier Sciences Publishers Ltd. (UK), pp. 291-294.

Kibbe, Arthur H. (Editor), "Benzyl Alcohol", Handbook of Pharmaceutical Excipients, Third Edition, American Pharmaceutical Association, 2000, pp. 41-43.

Marana, R. et al., "Influence of the Purity of the Iodinated Tracer on the Specificity of the Radioimmunoassay of Human Follicle-Stimulating Hormone", Acta Endocrinologica, vol. 92, 1979, pp. 585-598.

Miyachi, Yukitaka, et al., "Structural Integrity of Gonadotropins after Enzymatic Iodination", Biochemical and Biophysical Research Communications, vol. 46, No. 3, 1972, pp. 1213-1221.

Mizutani, Takaharu et al., "Estimation of Adsorption of Drugs and Proteins on Glass Surfaces with Controlled Pore Glass as a Reference", Journal of Pharmaceutical Sciences, vol. 67., No. 8, Aug. 1978, American Pharmaceutical Association, pp. 1102-1105.

Mizutani, Takaharu, et al., "Study of Protein Adsorption on Glass Surfaces with a Hydrophobic Fluorescent Probe", Chem. Pharm. Bulletin, vol. 32, No. 6, 1984, pp. 2395-2400.

Pikal, Michael J. et al., "The Effects of Formulation Variables on the Stability of Freeze-Dried Human Growth Hormone", Pharmaceutical Research, vol. 8, No. 4, 1991, pp. 427-436.

Pinto, Heidi et al., "Preparation of High-Quality Iodine-125-Labelled Pituitary Human Follicle-Stimulating Hormone (hFSH) For Radioimmunoassay: Comparison of Enzymatic and Chloramine-T Iodination", Clinica Chimica Acta, Elsevier/North-Holland Biomedical Press, vol. 76, 1977, pp. 25-34.

Rathnam, P. et al., "Studies on Modification of Tryptophan, Methionine, Tyrosine and Arginine Residues of Human Follicle-Stimulating Hormone and Its Subunits", Biochimica et Biophysica Acta, vol. 576, 1979, Elsevier/North-Holland Biomedical Press, pp. 81-87.

Silberring, Jerzy et al., "A Universal and Simple Chloramine T Version for Hormone Iodination", International Journal of Applied Radiation and Isotopes, vol. 33, 1982, pp. 117-119.

Stankov, B. M. et al., "The Effect of the Purity of the Iodinated Tracer on the Specificity of a Homologous Assay of Ovine Follicle Stimulating Hormone", Biochemistry International, vol. 12, No. 1, Jan. 1986, pp. 11-19.

Suginami, H. et al., "Influence of the Purity of the Iodinated Tracer on the Specificity of the Radioimmunoassay of Human Luteinizing Hormone", Acta Endocrinologica, vol. 89, 1978, pp. 506-520.

Terada, Shigeyuki, "Iodination of Luteinizing Hormone-Releasing Hormone", Biochemistry 1980, vol. 19, pp. 2572-2576.

Van den Steen, Philippe et al., "Concepts and Principles of O-Linked Glycosylation", hCG papers / CTP extensions / Boime papers, Critical Reviews in Biochemistry and Molecular Biology, vol. 35, No. 3, 1998, pp. 151-208.

Wang, Yu-Chang John et al., "Review of Excipients and pH's for Parenteral Products Used in the United States", Journal of the Parenteral Drug Association, vol. 34, No. 6, Nov.-Dec. 1980, pp. 452-462.

Walsh, Gary, "Pharmaceutical biotechnology products approved within the European Union", European Journal of Pharmaceutics and Biopharmaceutics, vol. 55, 2003, pp. 3-10.

Waterman, Kenneth C. et al., "Stabilization of Pharmaceuticals to Oxidative Degradation", Pharmaceutical Development and Technology, vol. 7, No. 1, 2002, pp. 1-32.

Xing, Yongna et al., "Threading of a glycosylated protein loop through a protein hole: Implications for combination of human chorionic gonadotropin subunits", Protein Science, vol. 10, 2001, pp. 226-235.

* cited by examiner

FSH FORMULATION

CROSS-REFERENCE

This application is a continuation of U.S. application Ser. No. 09/928,198 filed on Aug. 10, 2001 now abandoned, which is a divisional of U.S. application Ser. No. 09/744,431 filed Jan. 22, 2001 now abandonded, which is the U.S. national stage application of International Application No. PCT/US99/16031 field Jul. 15, 1999, which claims the benefit of U.S. Provisional Application Nos. 60/093,906 filed Jul. 23, 1998; 60/094,611 filed Jul. 30, 1998, 60/094,767 filed Jul. 31, 1998; 60/098,711 filed Sep. 1, 1998; and 60/100,696 filed Sep. 17, 1998 each of which applications is entirely incorporated herein by reference.

FIELD OF INVENTION

This invention relates to new formulations, articles of manufacture and methods of using preparations of follicle stimulating hormone (FSH) or follicle stimulating hormone variants (FSH variants) known in the art. The invention also provides advantageous, multi-use and stable solutions and formulations and pharmaceutical products of which have not previously existed for therapeutic use. These formulations and products are particularly useful in therapeutic regimens for increasing serum levels of FSH or FSH variants over a period of treatment. Thus, inter alia, the invention fills the need for convenient stable and preserved solutions, formulations and products comprising FSH or FSH variants and using these formulations and products in the treatment of infertility.

BACKGROUND OF THE INVENTION

FSH is indicated for use in infertility. The patients are administered daily or twice daily intramuscular ("IM") or subcutaneous ("SC") injections with dosage adjusted to response, usually ranging from 75-300 IU/day. The short half-life of FSH makes it necessary that the patients are given once or twice daily injections, extending to several days, depending on their ovarian or testicular response. A more stable formulation of FSH or of a FSH variant would provide improvements for use in therapy.

Although FSH has not been previously administered by approved modes of administration other than by IM or SC, other therapeutic proteins are expected to be administered over an extended number of days. Various delivery methods, including regular SC or IM injections over a period of time, transdermal patches, implants, osmotic pumps, micropumps, cartridges, pulmonary delivery systems, and the like, would be useful, e.g., in facilitating patient compliance, to reducing discomfort, or to facilitating administration. These extended treatment regimens generally require stable solutions or preservatives in the formulation.

Preservatives, in one aspect, prevent or minimize deleterious microbial contamination in the formulation. For conventional, non-protein therapeutics, antimicrobial preservative agents, such as chlorohexidine, phenol, benzyl alcohol, m-cresol, o-cresol, p-cresol, chlorocresol, phenylmercuric nitrate, thimerosal, benzoic acid, alkylparaben (methyl, ethyl, propyl, butyl and the like), benzalkonium chloride, benzethonium chloride, sodium dehydroacetate and thimerosal and various mixtures thereof, are often added to a liquid formulation to ensure sterility during shelf life and/or the multiple use regimen (Akers, M J, Pharm. Technol. 8, 36-46, 1984; Gennnaro, A R., Remington's Pharmaceutical Sciences, 17$^{th}$ edition., Mack, Easton, Pa., 1278-1280, 1985). These preservatives as a class, however, tend to be detrimental to the stability of proteins. For example, a very effective preservative, m-cresol, has been reported to generally combine with and denature proteins (Development of Pharmaceutical Parenteral Dosage Forms, Bontempo, ed., Marcel Dekker, Inc., New York, N.Y., pp. 118-119, 1977). It also presents particular difficulty with the solution stability of hormones, such as human growth hormone (Maa Y F and Hsu C, International Journal of Pharmaceutics, 140, pp. 155-168, 1996).

FSH is a member of the heterodimer, glycoprotein hormone family that includes thyroid stimulating hormone (TSH), chorionic gonadotropin (CG), and lutenizing hormone (LH) (Pierce J G and Parsons T F, Annu. Rev. Biochem., 50, 465-495, 1981; Baenziger and Green, Biochem. Biophys. Acta., 947, 287-306, 1988). The members of this family are heterodimers, held together generally by noncovalent interactions between the two different subunits. The human FSH (hFSH) heterodimer consists of (i) a mature 92 amino acid alpha subunit, which also is common to the other human family members (i.e., chorionic gonadotropin ("CG"), leutinizing hormone ("LH") and thyroid stimulating hormone ("TSH")); and (ii) a mature 111 amino acid beta subunit that is unique to FSH (Shome et al., J. Clin. Endocrinol. Metab. 39:187-205 (1974); Shome, et al., J. Prot. Chem, 7:325-339, 1988). The alpha and beta subunits bind non-covalently and, thus, the binding was thought to be more susceptible to protein destabilizing agents.

The native human and other mammalian FSH alpha and beta amino acid sequences and certain variants of these sequences were well known in the art prior to 1982 and cloning and expression of active human and other mammalian FSH in mammalian cells had been accomplished prior to 1985. The common gonadotropin alpha (or FSH alpha) subunit was sequenced from purified protein (Bellisario et al., J. Biol. Chem. 248:6796 (1973); Morgan et al., J. Biol. Chem. 250:5247 (1975)) and later cloned and expressed (Fiddes et al., Nature 281:351 (1979); Nature 286:684 (1981); J. Molec. Appl. Genet. 1:3-18 (1981)). The FSH beta subunit was sequenced from purified protein (Shome et al., J. Clin Endocrinol. Metab. 39:187 (1974); Saxena et al., J. Biol. Chem. 251:993 (1976)); (Sairam et al., Biochem. J. 197:541 (1981); Fujiki et al., Biochem Biophys. Acta 624:428 (1980)). Integrated Genetics reported the recombinant expression of a human CG (Biotechnology Newswatch (p. 3, Jun. 20, 1983); Chemical and Engineering News 61:41 (Nov. 21, 1983); Genetic Technology News 3:9 (Dec. 12, 1983)) and in active form (Biotechnology Newswatch, Jan. 16, 1984)), and they also reported the successful cloning of FSH (Genetic Engineering Newsletter 4:4 (Aug. 10, 1984)) and recombinant FSH produced in mammalian cells in active form (DNA 4:76 (published Jan. 16, 1985)). Amgen also reported the expression of an active bovine LH in CHO cells (Proc. Natl. Acad. Sci. USA 82:7280 (November 1985)).

There is substantial evidence in the literature indicating that heterodimeric protein hormones can dissociate under physiological or acidic conditions (Ryan, R. J., et al., Recent Progr. Hormone Res. 26:105-137; 1970, Strickland, T W and Puett, D, J. Biol. Chem., 257:2954-2960; 1982, Reichert L E and Ramsey R B, J. Biol. Chem., 250:3034-3040; 1975). Intact dimers are essential for biological activity and vital to secretion of FSH (Baenziger J U and Green E D, Biochem. Biophys. Acta, 947:287-306, 1988; Corless, et al., J. Cell Biol., 104:1173-1181, 1987). Attempts to counteract the instability of FSH include those where a single chain molecule is produced, incorporating two subunits into one stable molecule, and those where additional disulfides bonds are created to stabilize the interaction between the two subunits (Sughara T., et al., J. Biol. Chem., 271:10445-10448, 1996; Heikoop J. C., et al., Nature Biotech, 15:658-62, 1997).

Donaldson, U.S. Pat. No. 5,162,306, is directed to veterinary compositions comprising FSH and LH. These compositions are shown to be stable in thymol (5-methyl-2(1-methylethyl)phenol). Donaldson reports that thymol is one preservative in the list of preservatives in the U.S. Pat. No. XXI that will not damage glycoprotein hormones (U.S. Pat. No. 5,162,306) in the disclosed SUPER-OV formulation.

Urinary derived FSH from postmenopausal women (hMG, marketed as Menotropin or Humagon™ by Organon and as urofollitropin or Metrodin™ by Serono) has been used as an injectable for over 30 years for the development of multiple follicles in ovulatory patients participating in Assisted Reproductive Technology (ART) programs and for the induction of ovulation in anovulatory infertile patients. (Fauser B C J M and Van Heusden A M, Endocrine Rev., 18, 71-106, 1997). More recently, CHO cell-derived recombinant human FSH (rhFSH) has become available (Keene J. L., et al., J. Biol. Chem., 264:4769-4752, 1989; Loumaye E., et al., Human Reprod. Update, 1:188-1999, 1995; Olijve W., et al., Mol. Hum. Reprod., 2:361-369, 1996).

Therapeutic FSH (either hMG or rhFSH) is currently supplied in a lyophilized form in ampules of 75 IU/vial and 150 IU/vial with a shelf life of one and a half to two years when stored at 2-25° C. Daily injections with starting doses of 75 IU or 150 IU are recommended for up to ten days to reach steady state concentrations of hFSH that are 1.5-2.5 times higher than that after a single dose administration. This dosing regime yields concentrations necessary for therapeutic efficacy, as FSH acts through a threshold mechanism (Schoemaker J., et al., Ann. NY. Acad. Sci. 687:296-299, 1993). Depending on the patient's response, up to three cycles of treatment with increasing doses of FSH can be used. The patient or the partner is required to reconstitute a new vial of lyophilized material with diluent and administer it immediately after reconstitution (Package insert N1700101A, published in February 1996, for Fertinex™ (urofollitropin for injection, purified) for subcutaneous injection, by Serono Laboratories, Inc., Randolph, Mass.) on a daily basis. Any unused material is discarded.

Accordingly, there remains a need in the art to increase patient compliance via the development of stable formulations and preserved formulations of FSH or FSH variant proteins, and related articles of manufacture. These stable preparations are especially needed where extended treatments are required or advised, such as fertility treatments with FSH. There is also need to provide an FSH or FSH variant products that can be used and approved for multi-use administration over a period of twenty-four hours or greater. The invention also provides new stable solutions and formulations and preserved solutions and formulations of FSH and FSH variants and the related articles of manufacture that can also be used and approved for use over a period of twenty-four hours or greater.

SUMMARY OF THE INVENTION

This invention provides new formulations of FSH or FSH variants, their preparation, and their pharmaceutical or veterinary use in the treatment of fertility disorders and related articles of manufacture.

In one aspect, the invention provides preserved solutions and formulations comprising FSH or a FSH variant and a preservative selected from the group consisting of at least one phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, and derivatives or mixtures thereof in an aqueous diluent. optionally, the preserved solutions and formulations contain a selected buffer and a salt.

In another aspect, the invention provides stable solutions and formulations comprising a FSH or a FSH variant and a selected buffer, which is preferably a phosphate buffer with saline or a chosen salt.

In another aspect, the invention provides for the treatment of infertility which comprises administering to a patient in need thereof the preserved formulation of FSH or a FSH variant in solution containing at least one preservative selected from the group consisting of a phenol, an m-cresol, a p-cresol, an o-cresol, a chlorocresol, a benzyl alcohol, an alkylparaben (methyl, ethyl, propyl, butyl and the like), benzalkonium chloride, benzethonium chloride, sodium dehydroacetate and thimerosal, at least one derivative thereof, or mixtures thereof.

In another aspect, the invention provides for the treatment of infertility which comprises administering to a patient in need thereof the stable formulation of FSH or a FSH variant in a stable solution, which is preferably a phosphate buffer with saline or a chosen salt.

Another aspect of the invention provides a process for preparing at least one multi-dose formulation of FSH or a FSH variant, comprising admixing FSH and at least one preservative selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, derivatives thereof, or mixtures thereof in an aqueous diluent.

Another aspect of the invention provides a process for preparing at least one stable formulation of FSH or a FSH variant, comprising admixing FSH or a FSH variant in stable solution or formulation, which is preferable a phosphate buffer with saline or a chosen salt.

This invention also provides an article of manufacture for human pharmaceutical use, comprising packaging material and a vial comprising a solution of FSH or a FSH variant and a preservative, wherein said packaging material comprises a label which indicates that such solution may be held over a period of twenty-four hours or greater for use. The invention further comprises an article of manufacture for human pharmaceutical use, comprising packaging material, a first vial comprising lyophilized FSH or a FSH variant, and a second vial comprising a preservative, wherein said packaging material comprises a label which instructs a patient to reconstitute the FSH or a FSH variant in the preservative solution to form a solution which may be held over a period of twenty-four hours or greater for use under conditions as further described herein.

This invention also provides an article of manufacture for human pharmaceutical use, comprising packaging material and a vial comprising a solution of FSH or a FSH variant and stable solution or formulation, which is preferable a phosphate buffer with saline or a chosen salt, wherein said packaging material comprises a label which indicates that such solution may be held over a period of twenty-four hours or greater for use.

The invention further comprises an article of manufacture for human pharmaceutical use, comprising packaging material, a first vial comprising lyophilized FSH or a FSH variant, and a second vial comprising a preservative, wherein said packaging material comprises a label which instructs a patient to reconstitute the FSH or a FSH variant in the preservative solution to form a solution which may be held over a period of twenty-four hours or greater for use under conditions as further described herein.

This invention also provides an article of manufacture for human pharmaceutical use, comprising packaging material and a vial comprising a lyophilized FSH or a FSH variant and a second stable solution or formulation, which is preferable a phosphate buffer with saline or a chosen salt, wherein said packaging material comprises a label which instructs a patient to reconstitute the FSH or a FSH variant in the stable solution to form a solution which may be held over a period of twenty-four hours or greater for use under conditions as further described herein.

DETAILED DESCRIPTION

The present invention, in one aspect, provides recombinant and/or purified or isolated FSH or a FSH variant solutions and formulations, articles of manufacture and methods of use or treatment, and pharmaceutical products that are unexpectedly stable and/or are suitable for extended or multiple use.

Utility

These FSH or FSH variant solutions and formulations, articles of manufacture, methods of use and treatment using a FSH or a FSH variant, with improved or more suitable properties or stability, are useful for infertility treatment in women and/or men. These formulations, articles of manufacture, are additionally suitable for use in injectable and alternative delivery systems, e.g., but not limited to, nasal, pulmonary, transmucosal, transdermal, oral, subcutaneous, intramuscular or parenteral sustained release, dry, or liquid formulation. The FSH or a FSH variant solutions and formulations provided may also have increase in vivo potency compared to known commercial products, alone or in combination with at least one additional gonadotropin, by preventing or reducing loss of activity or stability, or by improving any aspect of the effectiveness or desirability of administration, e.g., by at least one of mode, frequency, dosage, comfort, ease of use, biological activity in vitro or in vivo, and the like.

Citations

All publications or patents cited herein are each entirely incorporated herein by reference as they show the state of the art at the time of the present invention or the filing dates of the related patent applications cited herein. The following citations are entirely incorporated by reference: Ausubel, et al., ed., Current Protocols in Molecular Biology, John Wiley and Sons, NY (1987-1999); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley and Sons, N.Y. (1994-1999); Colligan et al., eds., Current Protocols in Protein Science, John Wiley and Sons, N.Y. (1998-1999).

Definitions

Follicle stimulating hormone "FSH", whether produced recombinantly or isolated, and follicle stimulating hormone variants "FSH variants" as defined herein are well-known in the art. FSH as used herein refers to the FSH produced as a full length mature protein which includes, but are not limited to human FSH or "hFSH", whether produced recombinantly or isolated from human sources (see Shome B., et al., J. Prot. Chem., 7:325-339, 1988; Saxena B. B. and Rathnam P., J. Biol. Chem., 251:993-1005, 1976; Watkins, et al., DNA, 6:205-212, 1987; Shome B. and Parlow A. F., J. Clin. Endocrinol. Metab., 39(1):203-205, 1974; and Beck, et al., DNA, 4:76, 1985; U.S. Pat. Nos. 5,405,945, and 5,639,640)—each citation incorporated by reference. The protein sequence of the human FSH alpha subunit is provided in SEQ ID NO: 5, and the protein sequence of the human FSH beta subunit is given in SEQ ID NO:6. Furthermore, various FSH variants are known or are understood from the art (see Shome, J. Clin. Endocrin. Metab 39:187 (1974); Saxena, J. Biol Chem 251 (4):993-1005 (1976); 1978; Sairam et al., Biochem J 197:541 (1981); additionally see Closset Eur. J. Biochem. 86:115-120; Fujiki, J. Biol. Chem. 253:5363-5368 (1978); Sairam, Biochem. J. 197:541-552 (1981)—each citation independently incorporated by reference). ***Prior-art FSH beta subunits would include the Saxena sequence as well as a genus of sequences implicated in Sairam's discussion of (a) evolutionarily conserved amino acids and (b) well-known and characterized errors in sequencing. Further, those of skill in the art recognize that the substitution of a prior art identified amino acid with (i) a chemically similar amino acid or (ii) an evolutionarily conserved amino acid would have no appreciable affect on the biological activity of an FSH heterodimer comprised of an hFSH beta subunit, thus modified.

In particular, Sairam's commentary on the Saxena hFSH sequence, as well as his discussion of amino acid substitutions identified between functional FSH molecules, defines a genus of FSH beta chain sequences in the prior art. More specifically, the 1981 Sairam publication identifies conserved amino acid sequences referring to publications by Saxena et al., Shome et al., Closset et al., and Fujiki et al. Sairam, Biochem J 197:541, 551 (1981). The prior art (1) evidences a preference for the FSH beta-chain sequence of Saxena over that of Shome; (2) addresses the issue of carboxy-terminal heterogeneity; (3) states that portions of the molecule affected by interspecies differences that are not essential for activity of the hormone and (4) highlights the guidance drawn from homologies between species and between the beta chains of the three, human glycoprotein hormones, FSH, LH and TSH.

C-terminal heterogeneity is reported for all the published sequences except for that of the porcine FSH-s, in which glutamic acid was the only C-terminal residue. For position 27, Saxena assigned one tryptophan residue to this position also found support in the evolutionary conservation demonstrated for a tryptophan at position 24 for FSH-B, among all prior art species. For positions 44 and 46, Saxena shows that, at position 44, the residue should be arginine instead of lysine and, at position 46, lysine instead of arginine. The porcine, equine and ovine sequences also reflected an evolutionary pressure to conserve the arginine at the position 44. The variations at three positions, 21, 22 and 44 involve a structurally conservative or evolutionarily-conserved ("homologous") substitutions, each of which possess bio-activity.

Each of the Sairam, Shome, and Closset references disclose residues isoleucine, serine at positions 21-22, while Saxena discloses leucine, threonine and Fujiki discloses isoleucine, threonine at these positions. Each of these disclosures is not only an evolutionarily conservative substitution, but also a structurally conservative substitution. The variation at position 41 between the aspartic acid disclosed by each of Sairam, Shome, Closset, and Fujiki and the asparagine disclosed by Saxena, Closset and Sairam involves two evolutionarily conserved residues, each of which provide bio-activity. These disclosures of conservative substitutions and evolutionarily conserved substitutions guide the skilled artisan to distinct FSH beta chain variants, within the hFSH-B chain genus.

The FSH variants referred to herein are the carboxy terminal deletions of the beta subunit that are shorter than the full length mature protein of SEQ ID NO:6. Carboxy terminal deletions of the human beta subunit are provided in SEQ IDS NOS: 11, 12, and 13. It is understood that the carboxy terminal variants of the beta chain form dimers with a known alpha subunit to form a FSH variant heterodimer. Additionally, a number of species of FSH are known, including but limited to porcine FSH (SEQ ID NOS: 7 and 8), horse FSH (SEQ ID NOS: 3 and 4), bovine FSH (SEQ ID NOS: 1 and 2), sheep FSH (SEQ ID NOS: 9 and 10), and those cited in Combarnous Y., Endocrine Reviews, 13 (4), 670-691, 1992;—herein incorporated by reference. Therein it is understood that one skilled in the art would be able to make and prepare other carboxy terminal variants from the given species as further provided herein.

FSH heterodimers or FSH variant heterodimers can be produced by any suitable method, such as recombinantly, by isolation or purification from natural sources as may be the case, or by chemical synthesis, or any combination thereof. Non-limiting examples FSH heterodimers and FSH variant heterodimers comprising one alpha subunit and one beta subunit include but are not limited to:

(a): α-subunit:
(SEQ ID NO:1)
FPDGEFTMQGCPECKLKENKYFSKPDAPIYQCMGCCFSRAYPTPARSKKTMLVPKN
ITSEATCCVAKAFTKATVMGNVRVENHTECHCSTCYYHKS β-subunit:
(SEQ ID NO:2)
RSCELTNITITVEKEECGFCISINTTWCAGYCYTRDLVYRDPARPNIQKTCTFKEL
VYETVKVPGCAHHADSLYTYPVATECHCSKCDSDSTDCTVRGLGPSYCSFREIKE (b): α-subunit:
(SEQ ID NO:3)
FPDGEFTTQDCPECKLRENKYFFKLGVPIYQCKGCCFSRAYPTPARSRKTMLVPKN
ITSESTCCVAKAFIRVTVMGNIKLENHTQCYCSTCYHHKI β-subunit:
(SEQ ID NO:4)
NSCELTNITIAVEKEGCGFCITINTTWCAGYCYTRDLVYKDPARPNIQKTCTFKEL
VYETVKVPGCAHHADSLYTYPVATACHCGKCNSDSTDCTVRGLGPSYCSFGDMKE (c): α-subunit:
(SEQ ID NO:5)
APDVQDCPECTLQENPFFSQPGAPILQCMGCCFSRAYPTPLRSKKTMLVQKNVTSE
STCCVAKSYNRVTVMGGFKVENHTACHCSTCYYHKS β-subunit:
(SEQ ID NO:6)
NSCELTNITIAIEKEECRFCISINTTWCAGYCYTRDLVYKDPARPKIQKTCTFKEL
VYETVRVPGCAHHADSLYTYPVATQCHCGKCDSDSTDCTVRGLGPSYCSFGEMKE (d): α-subunit:
(SEQ ID NO:7)
FPDGEFTMQGCPECKLKENKYFSKLGAPIYQCMGCCFSRAYPTPARSKKTMLVPKN
ITSEATCCVAKAFTKATVMGNARVENHTECHCSTCYYHKS β-subunit:
(SEQ ID NO:8)
NSCELTNITITVEKEECNFCISINTTWCAGYCYTRDLVYKDPARPNIQKTCTFKEL
VYETVKVPGCAHHADSLYTYPVATECHCGKCDSDSTDCTVRGLGPSYCSFSEMKE (e): α-subunit:
(SEQ ID NO:9)
FPDGEFTMQGCPECKLKENKYFSKPDAPIYQCMGCCFSRAYPTPARSKKTMLVPKN
ITSEATCCVAKAFTKATVMGNVRVENHTECHCSTCYYHKS β-subunit:
(SEQ ID NO:10)
RSCELTNITITVEKEECSFCISINTTWCAGYCYTRDLVYKDPARPNIQKACTFKEL
VYETVKVPGCAHHADSLYTYPVATECHCGKCDRDSTDCTVRGLGPSYCSFSDIRE (f): α-subunit:
(SEQ ID NO:5)
APDVQDCPECTLQENPFFSQPGAPILQCMGCCFSRAYPTPLRSKKTMLVQKNVTSE
STCCVAKSYNRVTVMGGFKVENHTACHCSTCYYHKS β-subunit:
(SEQ ID NO:11)
NSCELTNITIAIEKEECRFCISINTTWCAGYCYTRDLVYKDPARPKIQKTCTFKEL
VYETVRVPGCAHHADSLYTYPVATQCHCGKCDSDSTDCTVRGLGPSYCSFGE (g): α-subunit:
(SEQ ID NO:5)
APDVQDCPECTLQENPFFSQPGAPILQCMGCCFSRAYPTPLRSKKTMLVQKNVTSE
STCCVAKSYNRVTVMGGFKVENHTACHCSTCYYHKS -continued β-subunit:
(SEQ ID NO:12)
NSCELTNITIAIEKEECRFCISINTTWCAGYCYTRDLVYKDPARPKIQKTCTFKEL
VYETVRVPGCAHHADSLYTYPVATQCHCGKCDSDSTDCTVRGLGPSYCSFGEM (h): α-subunit:
(SEQ ID NO:5)
APDVQDCPECTLQENPFFSQPGAPILQCMGCCFSRAYPTPLRSKKTMLVQKNVTSE
STCCVAKSYNRVTVMGGFKVENHTACHCSTCYYHKS β-subunit:
(SEQ ID NO:13)
NSCELTNITIAIEKEECRFCISINTTWCAGYCYTRDLVYKDPARPKIQKTCTFKEL
VYETVRVPGCAHHADSLYTYPVATQCHCGKCDSDSTDCTVRGLGPSYCSFGEMK The use of the term "recombinant" refers to recombinant preparations of FSH or FSH variants through the use of recombinant DNA technology (e.g. Boine et al., Seminars in Reproductive Endocrinology 10, 45-50, 1992, and as generally further provided and exemplified herein). The sequences for genomic and cDNA clones are known for the alpha and beta subunits of several species (Fiddes, J. C., et al., J of Mol. and Applied Genetics, 1:3-18(1981); Esch F. S., et al. DNA 5:363-369(1986); Watkins P. C., et al., DNA 6:205-212 (1987); Hirai T., et al., J. Mol. Endrocrinol. 5:147-158(1990); Maurer, R. A., et al., Mol. Endocrinol. 1:717-723(1987); Guzman K., et al., DNA Cell Biol. 10:593-601(1991); Kumar T R, et al., Gene. Dec. 12, 1995; 166(2):335-6; Kumar T R, et al., Gene. Dec. 12, 1995; 166(2):333-4—herein, each citation incorporated by reference). Several of the DNA sequences for alpha and beta subunits are provided as SEQ IDS: 14-20. Moreover, transfection of eucaryotic cells with the DNA sequences encoding a alpha and beta subunit, whether provided on one vector or on two vectors with each subunit having a separate promoter are capable of providing intact dimers, or by other methods understood in the art.

The FSH or a FSH variant used in accordance with the present invention may be produced not only by recombinant means, including from mammalian cell or transgenic preparations, but also may be purified from other biological sources, such as from urinary sources. Acceptable methodologies include those described in Hakola, K. Molecular and Cellular Endocrinology, 127:59-69, 1997; Keene, et al., J. Biol. Chem., 264:4769-4775, 1989; Cerpa-Poljak, et al., Endocrinology, 132:351-356, 1993; Dias, et al., J. Biol. Chem., 269:25289-25294, 1994; Flack, et al., J. Biol. Chem., 269:14015-14020, 1994; and Valove, et al., Endocrinology, 135:2657-2661, 1994, and U.S. Pat. No. 3,119,740, herein entirely incorporated by reference.

"Substantially pure," used in reference to a peptide or protein, means separation from other cellular and non-cellular molecules, including other protein molecules. A substantially pure preparation would be about at least 85% pure; preferably about at least 95% pure. A "substantially pure" protein can be prepared by a variety of techniques, well known to the skilled artisan, including, for example, high pressure liquid chromatography (HPLC) and as further understood in the art or demonstrated herein.

The term "administer" or "administering" means to introduce a formulation of the present invention into the body of a patient in need thereof to treat a disease or condition.

The term "patient" means a mammal that is treated for a disease or condition. Patients are of, but not limited to, the following origin, human, ovine, porcine, equine, bovine, rabbit and the like.

The term "alkylparaben" refers to a physiologically tolerated C1-C6 alkyl paraben useful as an antimicrobial agent. Non-limiting examples include at least one methylparaben, ethylparaben, propylparaben, and butylparaben.

The term "aqueous diluent" refers to a liquid solvent that contains water. Aqueous solvent systems may be comprised solely of water, or may be comprised of water plus one or more miscible solvents, and may contain dissolved solutes such as sugars or other excipients. The more commonly-used miscible solvents are the short-chain organic alcohols, such as, methanol, ethanol, propanol, short-chain ketones, such as acetone, and poly Alcohols, such as glycerol.

An "isotonicity agent" is a compound that is physiologically tolerated and imparts a suitable tonicity to a formulation to prevent the net flow of water across cell membranes that are in contact with the formulation. Compounds, such as glycerin, are commonly used for such purposes at known concentrations. Other suitable isotonicity agents include, but are not limited to, amino acids or proteins (e.g., methionine or albumin), salts (e.g., sodium chloride), and sugars (e.g., dextrose, sucrose and lactose), and/or many others well known in the art, incorporated herein by reference.

The term "preservative" refers to a compound or compositions added to a formulation to act as an anti-microbial, anti-fungal, anti-mycoplasmal, anti-viral, anti-prion and/or anti-bacterial agent. A preserved FSH or FSH variant containing formulation of the present invention preferably meets statutory or regulatory guidelines for preservative effectiveness to be a commercially viable multi-use product. Suitable preservatives can include, but are not limited to, at least one of a benzalkonium chloride, a benzethonium chloride, a chlorohexidine, a phenol, a m-cresol, a benzyl alcohol, a alkyl paraben (methylparaben, ethylparaben, propylparaben, butylparaben, and the like), sodium dehydroacetate, an o-cresol, a p-cresol, a chlorocresol, a phenylmercuric nitrate, a thimerosal, a benzoic acid, and any mixture thereof of one or more preservatives. See, e.g., Wallhauser, K., Develop. Biol. Standard. 24, pp. 9-28 (Basel, S. Krager, 1974).

The term "phosphate buffer" refers to excipients that contain a phosphate ion. Generally phosphate buffers are prepared from the phosphoric acid, or salt of phosphoric acid, including but not limited to sodium and potassium salts. Several salts of phosphoric acid are known in the art, such as sodium and potassium monobasic, dibasic, and tribasic salts of the acid. Salts of phosphoric acid are also know to occur as hydrates of the occurring salt. Phosphate buffers may cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8, including about pH 7.0, pH 7.2, and 7.4.

Preferred ions are the sodium or potassium ions, occurring singularly or together in the solution, as for instance as occurs phosphate buffered saline (PBS). Phosphate saline buffers are well known in the art, such as Dulbecco's Phosphate buffered saline. Salt concentrations in total solution can vary between about 5 mM, 9.5 mM, 10 mM, 50 mM, 100 mM, 150 mM, 200 mM, 250 mM, and 500 mM. Preferably the ion concentration is above 10 mM, or above 50 mM, or above 100 mM.

The term "vial" refers broadly to a reservoir suitable for retaining the FSH and diluent in a contained sterile state. Examples of a vial as used herein include ampules, cartridges, blister packages, or other such reservoir suitable for delivery of the FSH to the patient via pump (including osmotic), catheter, transdermal patch, cartridge, pulmonary, transmucosal, or parenteral delivery. Vials suitable for packaging products for parenteral, pulmonary, transmucosal, or transdermal administration are well-known and recognized in the art.

The term "stability" refers to the physical, chemical, and conformational stability of formulations of FSH of the present invention. Instability of a protein formulation may be caused by chemical degradation or aggregation of the protein molecules to form higher order polymers, by dissociation of the heterodimers into monomers, deglycosylation, modification of glycosylation or any other structural modification that reduces at least one biological activity of an FSH polypeptide included in the present invention.

A "stable" solution or formulation, which is preferable a phosphate buffer with saline or a chosen salt, is one wherein the degree of degradation, modification, aggregation, loss of biological activity and the like, of proteins therein is acceptably controlled, and does not increase unacceptably with time. Stability may be assessed by methods well-known in the art, including measurement of a sample's light scattering, apparent attenuation of light (absorbance, or optical density), size (e.g. by size exclusion chromatography), in vitro or in vivo biological activity and/or properties by differential scanning calorimetry (DSC). Other methods for assessing stability are well known in the art and can also be used according to the present invention.

The term "treating" refers to the administration, follow up, management and/or care of a patient for which FSH administration is desirable for the purpose of follicle or testicular stimulation or any other physiological response regulated by FSH. Treating can thus include, but is not limited to, the administration of FSH for the induction or improvement of sperm or follicular development or for ovulation induction. In addition, treatments for restoring normal spermatogenesis are contemplated in males.

A "salt" is a physiologically-acceptable salt of FSH. Such salts formed between any one or more of the charged groups in the protein and any one or more physiologically-acceptable, non-toxic cations or anions. Organic and inorganic salts include, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like, or for example, ammonium, sodium, potassium, calcium, or magnesium. Additional and suitable salts are known in the art and are included herein.

The term "buffer" or "physiologically-acceptable buffer" refers to a compound that is known to be safe for pharmaceutical or veterinary use in formulations and that has the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino-2-hydroxymethyl-1,3,-propanediol, and to any pharmacologically acceptable salt thereof. Preferable buffers are phosphate buffers with saline or an acceptable salt. Other buffers that are physiologically acceptable, and that are suitable for controlling pH at the desired level are known to those of ordinary skill in the art and are included herein.

Nucleic Acids Encoding for FSH and FSH Variants

A cDNA or genomic library can be screened using a probe based upon the sequence of a polynucleotide or known nucleic acid to obtain a clone encoding a known FSH sequence. Probes may be used to hybridize with genomic DNA or cDNA sequences to isolate homologous DNA sequences in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%; however, it should be understood that minor sequence variations in the probes and primers may be compensated for by reducing the stringency of the hybridization and/or wash medium.

Methods of amplification of RNA or DNA are well known in the art and can be used according to the present invention without undue experimentation, based on the teaching and guidance presented herein. Methods of selective amplification by PCR allow for the engineering of smaller segments of nucleic acid sequences, such as those that would encode a defined FSH variant beta chain. Such amplification techniques allow adding convenient termination signals, restrictions sites and the like to the amplified sequence.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification which uses antisense RNA to the target sequence as a template for double-stranded DNA synthesis (U.S. Pat. No. 5,130,238 to Malek, et al, with the trade name NASBA), Ausubel, supra; Colligan, supra, Sambrook, supra, the entire contents of which are herein incorporated by reference.

For instance, polymerase chain reaction (PCR) technology can be used to amplify the sequences of polynucleotides and related DNA sequences directly from genomic DNA or cDNA libraries. PCR and other in vitro amplification methods may also be useful, for example, to clone nucleic acid sequences that code for proteins to be expressed as, for example, to obtain any one of the provided FSH or FSH variants, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

Synthetic Methods for Constructing Nucleic Acids

Nucleic acids required to express any one of the given FSH or FSH variants can also be prepared by direct chemical synthesis by methods such as the phosphotriester method of Narang, et al., Meth. Enzymol. 68:90-99 (1979); the phosphodiester method of Brown, et al., Meth. Enzymol. 68:109-151 (1979); the diethylphosphoramidite method of Beaucage, et al., Tetra. Letts. 22:1859-1862 (1981); the solid phase phosphoramidite triester method described by Beaucage and Caruthers, Tetra. Letts. 22(20):1859-1862 (1981), e.g., using an automated synthesizer, e.g., as described in Needham-VanDevanter, et al., Nucleic Acids Res. 12:6159-6168 (1984); and the solid support method of U.S. Pat. No. 4,458,066. Chemical synthesis generally produces a single-stranded oligonucleotide, which may be converted into double-stranded DNA by hybridization with a complementary sequence, or by polymerization with a DNA polymerase using the single strand as a template. One of skill in the art will recognize that while chemical synthesis of DNA is limited to sequences of about 100 bases, longer sequences may be obtained by the ligation of shorter sequences.

Recombinant Expression Cassettes

As known in the art one can use recombinant expression cassettes to express known encoding nucleic acids for a known FSH or FSH variant. A nucleic acid sequence, for example a cDNA or a genomic sequence encoding a full-length subunit can be used to construct a recombinant expression cassette which can be introduced into a desired host cell. However, it is appreciated in the art that to obtain functional heterodimers one must express both subunits, whether from one plasmid or introduced on separate plasmids. A recombinant expression cassette will typically comprise a polynucleotide operably linked to transcriptional initiation regulatory sequences that will direct the transcription of the polynucleotide in the intended host cell for each subunit. Such methods are well known in the art to express FSH (e.g. CHO cell-derived recombinant human FSH (rhFSH); (Keene J. L., et al., J. Biol. Chem., 264:4769-4752, 1989; Loumaye E., et al., Human Reprod. Update, 1:188-1999, 1995; Olijve W., et al., Mol. Hum. Reprod., 2:361-369, 1996).

Both heterologous and non-heterologous (i.e., endogenous) promoters can be employed to direct expression of the nucleic acids encoding FSH or FSH variant subunits. General production methodologies by recombinant techniques are well known in the art. See, e.g., Sambrook, et al., 1989; Ausubel, et al., 1987-1989, each entirely incorporated herein by reference.

Vectors and Host Cells

Encoded polynucleotides for the alpha and beta subunits for FSH or an FSH variant can be joined to a vector containing a selectable marker for propagation in a host. Generally, a plasmid vector (or vectors if alpha and beta subunits are contained on separate expression vectors), is introduced in a precipitate, such as a calcium phosphate precipitate, or in a complex with a charged lipid. If the vector(s) is a virus, it can be packaged in vitro using an appropriate packaging cell line and then transduced into host cells.

The DNA insert for each subunit should be operatively linked to an appropriate promoter, such as the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated.

Expression vector(s) will preferably include at least one selectable marker. Such markers include, e.g., dihydrofolate reductase or neomycin resistance for eucaryotic cell culture, and tetracycline or ampicillin resistance genes for culturing in E. coli and other bacteria. Representative examples of appropriate hosts include, but are not limited to fungal cells, such as yeast cells; insect cells such as *Drosophila* S2 and *Spodoptera* Sf9 cells; animal or mammalian cells such as, but not limited to, CHO, COS, AV-12, HEPG2, NIH3T3 and Bowes melanoma cells; and plant cells, with CHO cells preferred. Appropriate culture mediums and conditions for the above-described host cells are known in the art. Preferred eucaryotic vectors include pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of a vector construct, or vectors, into a host cell can be effected by calcium phosphate transfection, DEAE-dextran mediated transfection, cationic lipid-mediated transfection, electroporation, transduction, infection or other methods. Such methods are described in many standard laboratory manuals, such as Sambrook, supra, Chapters 1-4 and 16-18; Ausubel, supra, Chapters 1, 9, 13, 15, 16.

It is anticipated that FSH or a FSH variant subunits can be expressed in a modified form, such as a fusion protein, and can include not only secretion signals, but also additional heterologous functional regions. For instance, a region of additional amino acids, particularly charged amino acids, can be added to the N-terminus of a polypeptide to improve stability and persistence in the host cell, during purification, or during subsequent handling and storage. Also, peptide moieties can be added to a polypeptide to facilitate purification. Such regions it is anticipated can be removed prior to final preparation of the desired FSH or a FSH variant. Such methods are generally described in many standard laboratory manuals, such as Sambrook, supra, Chapters 17.29-17.42 and 18.1-18.74; Ausubel, supra, Chapters 16, 17 and 18.

Expression of Proteins in Host Cells

Using nucleic acids sequences provided herein or known in the art, one may express the alpha and beta subunits of FSH or a FSH in a recombinantly engineered eucaryotic cell, such as mammalian cells. It is expected that those of skill in the art are knowledgeable in the numerous expression systems available for expression of a nucleic acid encoding a protein that contains two subunits. No attempt to describe in detail the various methods known for the expression of proteins in eucaryotes will be made.

In brief summary, the expression of isolated nucleic acids encoding a known FSH or a FSH variant will typically be achieved by operably linking separately the alpha subunit and the beta subunit DNA or cDNA to a promoter (which is either constitutive or inducible), followed by incorporation into an expression vector(s). Alternative, by inserting the DNA the vector will provide a suitable promoter. The vector(s) can be suitable for replication and integration in eucaryotic cells. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill in the art would recognize that modifications can be made without diminishing its biological activity. Some modifications may be made to facilitate the cloning, expression, or incorporation of the targeting molecules into the genome. Such modifications are well known to those of skill in the art and include, for example, providing conveniently located restriction sites or termination codons or purification sequences.

Alternatively, nucleic acids can be expressed in a host cell by turning on (by manipulation) in a host cell that contains endogenous DNA encoding the desired alpha and beta subunits. Such methods are well known in the art, e.g., as described in U.S. Pat. Nos. 5,580,734, 5,641,670, 5,733,746, and 5,733,761, entirely incorporated herein by reference.

Expression in Eucaryotes

A variety of eucaryotic expression systems such as mammalian cells, are known to those of skill in the art. As explained briefly below, a nucleic acid encoding for the alpha and beta subunit of a known FSH or a FSH variant can be expressed in these eucaryotic systems.

Synthesis of heterologous proteins in yeast is well known. F. Sherman, et al., Methods in Yeast Genetics, Cold Spring Harbor Laboratory (1982) is a well-recognized work describing the various methods available to produce the protein in yeast. Two widely utilized yeast for production of eucaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

The sequences encoding the alpha and beta subunits of FSH or a FSH variant can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines, with CHO cell lines preferred, such as CHO K1 from Lonza. Expression vectors for these cells can include expression control sequences, such as an origin of replication, a promoter (e.g., preferably the CMV promoter, a HSV tk promoter, EF1 alpha promoter, late or early SV40 promoter, or pgk (phosphoglycerate kinase) promoter), an enhancer (Queen, et al., Immunol. Rev. 89:49 (1986)), and processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992). Preferred host cells include CHO cells, such as CHO-K1 and preferred vectors include GS vectors, each available, e.g., from Lonza Biologics PLC (Slough, Berkshire, England, UK).

Appropriate vectors for expressing the alpha and beta subunit of FSH or a FSH variant in insect cells are usually derived from the SF9 baculovirus. Suitable insect cell lines include mosquito larvae, silkworm, armyworm, moth and *Drosophila* cell lines such as a Schneider cell line (See Schneider, J. Embryol. Exp. Morphol. 27:353-365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., J. Virol. 45:773-781 (1983)). Additionally, gene sequences to control replication in the host cell may be incorporated into the vector such as those found in bovine papilloma virus type-vectors. M. Saveria-Campo, Bovine Papilloma Virus DNA, a Eucaryotic Cloning Vector in DNA Cloning Vol. II, a Practical Approach, D. M. Glover, Ed., IRL Press, Arlington, Va., pp. 213-238 (1985).

Protein Purification

FSH or a FSH variant, once expressed, can be isolated from the cells by applying standard protein isolation techniques to the lysates. The monitoring of the purification process can be accomplished by using Western blot techniques or radioimmunoassay of other standard immunoassay techniques.

FSH or a FSH variant, containing an alpha and beta subunit, can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, size exclusion chromatography, and lectin chromatography. Preferably, high performance liquid chromatography ("HPLC"), cation exchange chromatography, affinity chromatography, size exclusion chromatography, or combinations thereof, are employed for purification. FSH and FSH variants having an alpha and beta subunit include naturally purified products, products of chemical synthetic procedures, and include products produced by recombinant techniques from a eucaryotic host, including, for example, yeast, higher plant, insect and mammalian cells. Depending upon the host employed in a recombinant production procedure, the polypeptides of the present invention can be glycosylated or can be non-glycosylated. Preferred FSH or a FSH variant molecules are glycosylated as would occur in eucaryotic hosts. In addition, polypeptides of the invention can also include an initial modified methionine residue, in some cases as a result of host-mediated processes. Such methods are described in many standard laboratory manuals, such as Sambrook, supra, Chapters 17.37-17.42; Ausubel, supra, Chapters 10, 12, 13, 16, 18 and 20, entirely incorporated herein by reference.

FBH or a FSB Variant And Polypeptides

FSH or a FSH variant known in the art, include but are not limited to those protein sequences listed in the sequence identification portion of the specification of which are further identified below:

SEQ ID NO: 1; bovine alpha subunit—96 amino acids
SEQ ID NO: 2; bovine beta subunit—111 amino acids
SEQ ID NO: 3; equine alpha subunit—96 amino acids
SEQ ID NO: 4; equine beta subunit—111 amino acids
SEQ ID NO: 5; human alpha subunit—92 amino acids
SEQ ID NO: 6; human beta subunit—111 amino acids
SEQ ID NO: 7; porcine alpha subunit—96 amino acids
SEQ ID NO: 8; porcine beta subunit—111 amino acids
SEQ ID NO: 9; ovine alpha subunit—96 amino acids
SEQ ID NO: 10; ovine beta subunit—111 amino acids
SEQ ID NO: 11; human beta variant—108 amino acids
SEQ ID NO: 12; human beta variant—109 amino acids
SEQ ID NO: 13; human beta variant—110 amino acids FSH or a FSH Variant Nucleotide Sequences FSH or a FSH variant nucleotide sequence, include but are not limited to those nucleotide sequences which encode an alpha or a beta subunit listed in the sequence identification portion of the specification of which are further identified below:

SEQ ID NO:14; human alpha cDNA—276 nucleotides (codes 92 amino acids)
SEQ ID NO:15; h. beta variant cDNA—324 nucleotides (codes 108 amino acids)
SEQ ID NO:16; h. beta variant cDNA—327 nucleotides (codes 109 amino acids)
SEQ ID NO:17; h. beta variant cDNA—330 nucleotides (codes 110 amino acids)
SEQ ID NO:18; h. beta cDNA—333 nucleotides (codes 111 amino acids)
SEQ ID NO:19; human alpha cDNA—276 nucleotides (codes 92 amino acids)
SEQ ID NO:20; h. beta variant cDNA—324 nucleotides (codes 108 amino acids)

The DNA of SEQ ID NO:19 and 20 is designed and constructed from ligated oligonucleotides. The differences between SEQ ID NO:19 and SEQ ID NO:14 are one that do not change the encoded amino acid sequence of the alpha subunit protein. Likewise, the differences between SEQ ID NO:20 and SEQ ID NO:15 are ones that do not change the encoded amino acid sequence of the beta variant subunit protein.

Amino Acid Codes

The amino acids that make up the proteins and polypeptides of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON (S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

Formulations

As noted above, the invention provides for stable formulations, which is preferable a phosphate buffer with saline or a chosen salt, as well as preserved solutions and formulations containing a preservative as well as multi-use preserved formulations suitable for pharmaceutical or veterinary use, comprising FSH or FSH variant in a pharmaceutically acceptable formulation. Preserved formulations contain at least one preservative selected from the group consisting of at least one phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof in an aqueous diluent.

As noted above, the invention provides an article of manufacture, comprising packaging material and a vial comprising a solution of FSH or a FSH variant with the prescribed buffers and/or preservatives, optionally in an aqueous diluent, wherein said packaging material comprises a label which indicates that such solution may be held over a period of twenty-four hours or greater. The invention further comprises an article of manufacture, comprising packaging material, a first vial comprising lyophilized FSH or a FSH variant, and a second vial comprising an aqueous diluent of prescribed buffer or preservative, wherein said packaging material comprises a label which instructs a patient to reconstitute the FSH or a FSH variant in the aqueous diluent to form a solution which may be held over a period of twenty-four hours or greater.

The FSH or a FSH variant used in accordance with the present invention may be produced by recombinant means, including from mammalian cell or transgenic preparations, or may be purified from other biological sources, such as from urinary sources. Acceptable methodologies include those described in Hakola, K. Molecular and Cellular Endocrinology, 127:59-69, 1997; Keene, et al., J. Biol. Chem., 264: 4769-4775, 1989; Cerpa-Poljak, et al., Endocrinology, 132: 351-356, 1993; Dias, et al., J. Biol. Chem., 269:25289-25294, 1994; Flack, et al., J. Biol. Chem., 269:14015-14020, 1994; and Valove, et al., Endocrinology, 135:2657-2661, 1994, and U.S. Pat. No. 3,119,740, herein entirely incorporated by reference.

The method by which the proteins are provided for the formulations of this invention is not particularly relevant. Preferably FSH is a heterodimer comprising one alpha subunit and one beta subunit, respectfully, as provide in SEQ ID NOS 5 and 6, or a FSH variant heterodimer comprising one alpha subunit and one beta subunit, respectfully, as given in SEQ ID NOS: 5 and 11; 5 and 12; and 5 and 13. Suitable FSH or a FSH variant species within the present invention include, but are not limited to, at least one known alpha subunit sequence and at least one known beta subunit (see sequence listing for known alpha and beta subunits and as otherwise known in the art).

Non-limiting examples of FSH or a FSH variant, include but are not limited to:

```
(a): α-subunit:
                                                    (SEQ ID NO:1)
     FPDGEFTMQGCPECKLKENKYFSKPDAPIYQCMGCCFSRAYPTPARSKKTMLVPKN
     ITSEATCCVAKAFTKATVMGNVRVENHTECHCSTCYYHKS β-subunit:
                                                    (SEQ ID NO:2)
     RSCELTNITITVEKEECGFCISINTTWCAGYCYTRDLVYRDPARPNIQKTCTFKEL
     VYETVKVPGCAHHADSLYTYPVATECHCSKCDSDSTDCTVRGLGPSYCSFREIKE (b): α-subunit:
                                                    (SEQ ID NO:3)
     FPDGEFTTQDCPECKLRENKYFFKLGVPIYQCKGCCFSRAYPTPARSRKTMLVPKN
     ITSESTCCVAKAFIRVTVMGNIKLENHTQCYCSTCYHHKI β-subunit:
                                                    (SEQ ID NO:4)
     NSCELTNITIAVEKEGCGFCITINTTWCAGYCYTRDLVYKDPARPNIQKTCTFKEL
     VYETVKVPGCAHHADSLYTYPVATACHCGKCNSDSTDCTVRGLGPSYCSFGDMKE (c): α-subunit:
                                                    (SEQ ID NO:5)
     APDVQDCPECTLQENPFFSQPGAPILQCMGCCFSRAYPTPLRSKKTMLVQKNVTSE
     STCCVAKSYNRVTVMGGFKVENHTACHCSTCYYHKS β-subunit:
                                                    (SEQ ID NO:6)
     NSCELTNITIAIEKEECRFCISINTTWCAGYCYTRDLVYKDPARPKIQKTCTFKEL
     VYETVRVPGCAHHADSLYTYPVATQCHCGKCDSDSTDCTVRGLGPSYCSFGEMKE (d): α-subunit:
                                                    (SEQ ID NO:7)
     FPDGEFTMQGCPECKLKENKYFSKLGAPIYQCMGCCFSRAYPTPARSKKTMLVPKN
     ITSEATCCVAKAFTKATVMGNARVENHTECHCSTCYYHKS β-subunit:
                                                    (SEQ ID NO:8)
     NSCELTNITITVEKEECNFCISINTTWCAGYCYTRDLVYKDPARPNIQKTCTFKEL
     VYETVKVPGCAHHADSLYTYPVATECHCGKCDSDSTDCTVRGLGPSYCSFSEMKE (e): α-subunit:
                                                    (SEQ ID NO:9)
     FPDGEFTMQGCPECKLKENKYFSKPDAPIYQCMGCCFSRAYPTPARSKKTMLVPKN
     ITSEATCCVAKAFTKATVMGNVRVENHTECHCSTCYYHKS β-subunit:
                                                   (SEQ ID NO:10)
     RSCELTNITITVEKEECSFCISINTTWCAGYCYTRDLVYKDPARPNIQKACTFKEL
     VYETVKVPGCAHHADSLYTYPVATECHCGKCDRDSTDCTVRGLGPSYCSFSDIRE (f): α-subunit:
                                                    (SEQ ID NO:5)
     APDVQDCPECTLQENPFFSQPGAPILQCMGCCFSRAYPTPLRSKKTMLVQKNVTSE
     STCCVAKSYNRVTVMGGFKVENHTACHCSTCYYHKS β-subunit:
                                                   (SEQ ID NO:11)
     NSCELTNITIAIEKEECRFCISINTTWCAGYCYTRDLVYKDPARPKIQKTCTFKEL
```

-continued
```
VYETVRVPGCAHHADSLYTYPVATQCHCGKCDSDSTDCTVRGLGPSYCSFGE
```

(g): α-subunit:
(SEQ ID NO:5)
```
APDVQDCPECTLQENPFFSQPGAPILQCMGCCFSRAYPTPLRSKKTMLVQKNVTSE
STCCVAKSYNRVTVMGGFKVENHTACHCSTCYYHKS
```

β-subunit:
(SEQ ID NO:12)
```
NSCELTNITIAIEKEECRFCISINTTWCAGYCYTRDLVYKDPARPKIQKTCTFKEL
VYETVRVPGCAHHADSLYTYPVATQCHCGKCDSDSTDCTVRGLGPSYCSFGEM
```

(h): α-subunit:
(SEQ ID NO:5)
```
APDVQDCPECTLQENPFFSQPGAPILQCMGCCFSRAYPTPLRSKKTMLVQKNVTSE
STCCVAKSYNRVTVMGGFKVENHTACHCSTCYYHKS
```

β-subunit:
(SEQ ID NO:13)
```
NSCELTNITIAIEKEECRFCISINTTWCAGYCYTRDLVYKDPARPKIQKTCTFKEL
VYETVRVPGCAHHADSLYTYPVATQCHCGKCDSDSTDCTVRGLGPSYCSFGEMK
```

The range of protein hormone in the product of the present invention includes amounts yielding upon reconstitution, if in a wet/dry system, concentrations from about 1.0 µg/ml to about 50 mg/ml, although lower and higher concentrations are operable and are dependent on the intended delivery vehicle, e.g., solution formulations will differ from transdermal patch, pulmonary, transmucosal, or osmotic or micro pump methods. The hormone concentrations are preferably about 5.0 µg/ml to 2 mg/ml and most preferably about 5.0 µg/ml, or 10 µg/ml, or 50 µg/ml to about 200 µg/ml.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. Preferably, the preservative is meta-cresol, phenol, chlorocresol, or a mixture thereof, with m-cresol most preferred. The concentration of preservative used in the formulation is a concentration sufficient to yield an anti-microbial effect. Such concentrations are dependent on the preservative selected and are readily determined by the skilled artisan. For example, m-cresol or phenol (alone or in combination) are generally at a concentration from about 23 mM to about 35 mM. Surprisingly, the preservatives used in the presently claimed formulations do not adversely affect the biological activity of FSH or a FSH variant and allow multi-use administration.

Other excipients, e.g. isotonicity agents, buffers, antioxidants, preservative enhancers, may be optionally and preferably added to the diluent. An isotonicity agent, such as glycerin, is commonly used at known concentrations. The concentration of glycerin is generally about 16 mg/ml. A physiologically tolerated buffer is preferably added to provide improved pH control. The formulations may cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA may optionally be added to the formulations or compositions to reduce aggregation. These additives are particularly useful if a pump or plastic container is used to administer the formulation. The presence of pharmaceutically acceptable surfactant mitigates the propensity for the protein to aggregate. The present claimed formulations are surprisingly stable. Prior to the present invention, the preparation of preserved, multi-use formulations of FSH was believed to be impossible due to instability. Applicants have discovered that the claimed formulations may be safely stored at temperatures of from about 2 to about 40° C. and retain the biologically activity of the protein for extended periods of time, exceeding 2 months and as further demonstrated.

The formulations of the present invention can be prepared by a process which comprises mixing FSH or a FSH variant and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the FSH or a FSH variant and preservative in an aqueous diluent is carried out using conventional dissolution and mixing procedures. To prepare a suitable formulation, for example, a measured amount of FSH or a FSH variant in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed formulations may be provided to patients as clear solutions or as dual vials comprising a vial of lyophilized FSH or a FSH variant that is reconstituted with a second vial containing a preservative and/or excipients, preferably a phosphate buffer and/or saline and a chosen salt, in an aqueous diluent. Either a single solution vial or dual vial requiring reconstitution may be reused multiple times and may suffice for a single or multiple cycles of patient treatment and thus provides a more convenient treatment regimen than currently available.

The present claimed articles of manufacture are surprisingly useful for administration over a period of twenty-four hours or greater. Prior to the present invention, such products were only suitable and approved for immediate use. The patient was instructed to discard unused material leading to waste and expense. Accordingly, the presently claimed articles of manufacture offer significant advantages to the patient. Applicants have discovered that the claimed formulations may be safely stored at temperatures of from about 2 to about 40° C. and retain the biologically activity of the protein for extended periods of time, exceeding 2 months; thus, allowing a package label indicating that the solution may be held and/or used over a period of 24, 36, 48, 72, or 96 hours or greater. If preserved diluent is used, such label may include use up to one, one and a half, to two years.

The solutions of FSH or a FSH variant in the invention can be prepared by a process which comprises mixing FSH or a FSH variant in an aqueous diluent. Mixing is carried out using conventional dissolution and mixing procedures. To prepare a suitable diluent, for example, a measured amount of FSH or a FSH variant in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed products may be provided to patients as clear solutions or as dual vials comprising a vial of lyophilized FSH or a FSH variant that is reconstituted with a second vial containing the aqueous diluent. Either a single solution vial or dual vial requiring reconstitution may be reused multiple times and may suffice for a single or multiple cycles of patient treatment and thus provides a more convenient treatment regimen than currently available.

The claimed products may be provided indirectly to patients by providing to pharmacies, clinics, or other such institutions and facilities, clear solutions or dual vials comprising a vial of lyophilized FSH or a FSH variant that is reconstituted with a second vial containing the aqueous diluent. The clear solution in this case may be up to one liter or even larger in size, providing a large reservoir from which smaller portions of the FSH or a FSH variant solution may be retrieved one or multiple times for transfer into smaller vials and provided by the pharmacy or clinic to their customers and/or patients. The diluent vial in this case may be up to one liter or even larger in size, providing a large reservoir from which smaller portions of the diluent may be retrieved multiple times for reconstitution of the lyophilized FSH or a FSH variant. The clear solution or reconstituted FSH or a FSH variant solution provided by the pharmacy or clinic to their customers and patients may suffice for single or multiple cycles of patient treatment and thus provides a more convenient treatment regimen than currently available.

Recognized devices comprising these single vial systems include those pen-injector devices for delivery of a solution such as Humaject®, NovoPen®, B-D®Pen, AutoPen®, and OptiPen®. Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product may be used. The packaging material of the present invention provides instructions to the patient to reconstitute the FSH or a FSH variant in the aqueous diluent to form a solution and to use the solution over a period of twenty-four hours or greater for the two vial, wet/dry, product. For the single vial, solution product, the label indicates that such solution may be used over a period of twenty-four hours or greater. The presently claimed products are useful for human pharmaceutical product use.

The formulations of the present invention can be prepared by a process which comprises mixing FSH or a FSH variant and a selected buffer, preferably a phosphate buffer containing saline or a chosen salt. Mixing the FSH or a FSH variant and buffer in an aqueous diluent is carried out using conventional dissolution and mixing procedures. To prepare a suitable formulation, for example, a measured amount of FSH or a FSH variant in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed stable or preserved formulations may be provided to patients as clear solutions or as dual vials comprising a vial of lyophilized FSH or a FSH variant that is reconstituted with a second vial containing a preservative or buffer and excipients in an aqueous diluent. Either a single solution vial or dual vial requiring reconstitution may be reused multiple times and may suffice for a single or multiple cycles of patient treatment and thus provides a more convenient treatment regimen than currently available.

FSH or a FSH variant in either the stable or preserved formulations or solutions described herein, may be administered to a patient in accordance with the present invention via a variety of delivery methods including SC or IM injection; transdermal, pulmonary, transmucosal, implant, osmotic pump, cartridge, micro pump, oral, or other means appreciated by the skilled artisan, as well-known in the art.

The following examples are provided merely to further illustrate the preparation of the formulations and compositions of the invention. The scope of the invention shall not be construed as merely consisting of the following examples.

NUCLEIC ACID/POLYPEPTIDE EXAMPLES

Example 1

Cloning and Expression of FSH or a FSH Variant, in Mammalian Cells

A typical mammalian expression vector contains at least one promoter element, which mediates the initiation of transcription of mRNA, the polypeptide coding sequence, and signals required for the termination of transcription and polyadenylation of the transcript. However, because functional FSH or FSH variants contain both an alpha and beta subunit, means to express both subunits are required, either by expressing both subunits from single vector containing a promoter element for each subunit, or by using two vectors: a first vector containing a promoter to express the first subunit and a second vector that has a promoter to express the second subunit.

Additionally, each mammalian expression vector have elements that may be present on one or more vectors include enhancers, Kozak sequences and intervening sequences flanked by donor and acceptor sites for RNA splicing.

Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in providing FSH or FSH variants subunits include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRS-Vcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the desired DNA sequences for the alpha and beta subunit can be expressed in stable cell lines that contain the DNA sequences for expressing each subunit once integrated into a chromosome(s). The co-transfection with a selectable marker such as dhfr, gpt, neomycin, or hygromycin allows the identification and isolation of the transfected cells as known in the art.

The transfected DNA sequences for the subunits can also be amplified to express large amounts of the encoded polypeptide. The DHFR (dihydrofolate reductase) marker is useful to develop cell lines that carry several hundred or even several thousand copies of the DNA sequences of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins and polypeptides.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the DNA sequences for the alpha and beta subunits of interest. The vectors contain in addition the 3' intron, the polyadenylation and termination signal of the rat preproinsulin gene.

Example 2

Cloning and Expression in COS or CHO Cells

An expression plasmid for FSH or a FSH variant is made by cloning a cDNA encoding FSH or a FSH variant subunits into the expression vector pcDNAI/Amp or pcDNAIII (which can be obtained from Invitrogen, Inc.). As previously mentioned, each subunit requires expression to produce a function heterodimer, either from independent introduction of separate vectors into the host cell or by engineering a single vector to express both alpha and beta subunits.

The expression vector(s) pcDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eucaryotic cells; (4) a CMV promoter, a polylinker, an SV40 intron; (5) several codons encoding a hemagglutinin fragment (i.e., an "HA" tag to facilitate purification) or HIS tag (see, e.g., Ausubel, supra) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin polypeptide described by Wilson, et al., Cell 37:767-778 (1984). The fusion of the HA tag to the target polypeptide, either the alpha or beta subunit, allows easy detection and recovery of the recombinant polypeptide with an antibody that recognizes the HA epitope. pcDNAIII contains, in addition, the selectable neomycin marker.

A DNA fragment encoding the alpha and beta subunit of FSH or a FSH variant, is separately cloned into the polylinker region of the vector so that recombinant polypeptide expression is directed by the CMV promoter. Insertion into the vector is optionally with or without the HA epitope. The plasmid construction strategy is as follows. The FSH or a FSH variant, cDNA of the deposited clone for each subunit is amplified using primers that contain convenient restriction sites.

The PCR amplified DNA fragment for each subunit and the vector, pcDNAI/Amp, are digested with suitable restriction enzyme(s) and then each subunit is ligated to digested vector. Each ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA for each subunit is isolated from resistant colonies and examined by restriction analysis or other means for the presence of the FSH or a FSH variant encoding fragment.

For expression of recombinant FSH or a FSH variant, COS cells are co-transfected with an expression vector for each subunit, as described above, using DEAE-DEXTRAN, as described, for instance, in Sambrook, et al., Molecular Cloning: a Laboratory Manual, Cold Spring Laboratory Press, Cold Spring Harbor, N.Y. (1989). Cells are incubated under conditions for expression of FSH or a FSH variant, by each vector.

It is expected that expression of the FSH HA or FSH variant HA fusion polypeptide is detected by radiolabeling and immunoprecipitation, using methods described in, for example Harlow, et al., Antibodies: A Laboratory Manual, 2nd Ed., Cold Spring Harbor Laboratory Press, Cold Spring Harbor, N.Y. (1988). To this end, two days after transfection, the cells are labeled by incubation in media containing 35S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson, et al. cited above. Proteins are precipitated from the cell lysate and from the culture media using an HA-specific monoclonal antibody. The precipitated protein is then are analyzed by SDS-PAGE and autoradiography. An expression product of the expected size is seen in the cell lysate, which is not seen in negative controls.

The vector pC4 is used for the expression of each subunit of FSH or a FSH variant. Alternatively, one skilled in the art would be able to adapt pC4 to express both alpha and beta subunits from a single vector. Plasmid pC4 is a derivative of the plasmid pSV2-dhfr (ATCC Accession No. 37146). The plasmid contains the mouse DHFR gene under control of the SV40 early promoter. Chinese hamster ovary—or other cells lacking dihydrofolate activity that are co-transfected with alpha and beta subunit plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If DNA sequences are linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained which contain the amplified DNA sequences integrated into one or more chromosome(s) of the host cell.

Plasmid pC4 contains for expressing the alpha and beta subunit DNA sequences of interest behind the strong promoter of the long terminal repeat (LTR) of the Rous Sarcoma Virus (Cullen, et al., Molec. Cell. Biol. 5:438-447 (1985)) which additionally contains a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the DNA sequences. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the FSH or a FSH variant, in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes can be used as well. Stable cell lines carrying the DNA sequences of the alpha and beta subunit integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete FSH or a FSH variant, for each subunit is amplified using PCR oligonucleotide primers corresponding to the 5' and 3' sequences of the gene. Non-limiting examples include 5' and 3' primers having nucleotides corresponding or complementary to a portion of the coding sequence of each subunit for an FSH or a FSH variant according to known methods in the art.

The amplified fragment(s) are digested with suitable endonucleases and then purified again on a 1% agarose gel. The isolated fragments for each subunit and the dephosphorylated vector are then separately ligated with T4 DNA ligase. *E. coli* HB101 or XL-1 Blue cells are then are separately transformed and bacteria are identified that contain the fragment (or fragments if the vector is adapted for expressing both alpha and beta subunits) inserted into plasmid pC4 using, for instance, restriction enzyme analysis.

Chinese hamster ovary (CHO) cells lacking an active DHFR gene are used for transfection. 5 μg of the expression plasmid(s) pC4 is cotransfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg/ml G418. After 2 days, the cells are trypsinized and seeded in hybridoma cloning plates (Greiner, Germany) in alpha minus MEM supplemented with 10, 25, or 50 ng/ml of methotrexate plus 1 μg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained which grow at a concentration of 100-200 mM. Expression of the desired product is analyzed, for instance, by SDS-PAGE and Western blot or by reverse phase HPLC analysis.

It will be clear that the invention can be practiced otherwise than as particularly described in the foregoing description and examples.

Numerous modifications and variations of the present methodologies is known in the art to expressing recombinant proteins, including those as described in Keene J. L., et al., J. Biol. Chem., 264:4769-4752, 1989; Loumaye E., et al., Human Reprod. Update, 1:188-1999, 1995; Olijve W., et al., Mol. Hum. Reprod., 2:361-369, 1996, as well as other recombinant techniques known and used for other gonadotropins.

Example 3

Expression in AV12 Cells

An expression cassett vector pGTH was used for expression of the alpha subunit in AV12. A number of published articles describe the use of AV12-664 and/or AV12-RGT18 cells (see Grinnell, B. W. et al., Blood 76(12):2546-54, 1990; Burck, P. J. et al., J. Biol. Chem. 265(9):5170-7, 1990; Parkinson, J. F. et al., J. of Biol. Chem. 265(21):12602-10, 1990; Grinnell, B. W. et al., J. Biol. Chem 266(15):9778-85, 1991; Wery, J. P. et al., Nature 352(6330):79-82, 1991; Berg, D. T. et al., Biotechniques 14:972-9, 1993; Gerlitz, B. et al. Biochemical Journal 295 (1):131-40, 1993; Kursar, J. D. et al. Molecular Pharmacology 46(2):227-34, 1994; Desai, M. A. et al. Molecular Pharmacology 48(4):648-57, 1995; Obesity Research 3 Suppl 4:4441S-4447S, 1995; Desai, M. A. et al. British Journal of Pharmacology 118(6):1558-64, 1996; Kumar, A. et al. Cancer Research 56(23):5397-402, 1996; Boggs, L. N. et al. J. of Neurochemistry 57(3):1324-7, 1996; Lucaites, V. L et al. Life Sciences 59(13):1081-95, 1996; Schoepp, D. D. et al. Neuropharmacology 35(12):1661-72, 1996; Kumar, A. et al. Cancer Research 57(15):3111-4, 1997; Urology 49(3):487-93, 1997; Wainscott, D. B. et al. Naunyn-Schmiedebergs Archives of Pharacology 357(1):17-24, 1998; Wu, S. et al. Brain Research—Molecular Brain Research 53(1-2):88-97, 1998. Similarly, publications have described use of the plasmid pGTH (see Grinnell, et al. J. Biol. Chem. 266(15):9778-85, 1991) and the plasmid pGTD (see Biolchemical Journal 295 (Pt1): 131-40, 1993.

Briefly, PGTH contains sequentially several elements: the SV40 early promoter.ori, E.coli hygromicin resistance, SV40 small "t" antigen splice site/poly-A site, pBR322 cloning remnant, BK virus (strain P2) cloning remnant, Poly-CA$_{20}$/GT$_{20}$ element (synthetic oligonucleotide), BK virus (strain P2) enhancer, AD2 major late promoter/spliced tripartite leader, BclI insertion site for the FSH alpha subunit coding sequence (including stop codon), SV40 small "t" antigen splice site/poly-A site; and pBR322 ampicillin resistance/ori.

The plasmid construct pGTH-alpha was generated to express the encoded the human alpha subunit sequence (SEQ ID:5) by cloning a 362-bp BclI FSH cDNA fragment into the unique BclI site of the vector (see sequence—SEQ ID:19 or 14). The FSH alpha cDNA fragment DNA was generated by PCR amplification using the shuttle plasmid pLGD637 as template (pLGD637 contains a synthetic/oligonucleotide-assembled FSH alpha cDNA sequence). The integrity of BclI insert was confired by sequencing followed by comparison to the GenPept database (Accession Number 31869).

An expression cassett vector pGTD was used to express the human beta subunit FSH variant sequence (SEQ ID:11). pGTD contains several elements for expression in AV12 cells. pGTD contains sequentially the BK virus (strain P2) cloning remnant, Poly-CA$_{20}$/GT$_{20}$ element (synthetic oligonucleotide), BK virus (strain P2) enhancer, AD2 major late promoter/spliced tripartite leader, Bcl1 insertion site for the FSH variant beta subunit coding sequence (including stop codon), SV40 small "t" antigen splice site/poly-A site; SV40 early promoter.ori, Murine dihydrofolate reductase cDNA, SV40 small "t" antigen splice site/poly-A site, and pBR322 ampicillin resistance/ori.

The plasmid construct pGTD-bCD3 was generated by cloning a 393-bp BclI FSH beta-bCD3 cDNA fragment into the unique BclI site of the pGTD vector (see SEQ ID:20 or 15). The FSH beta-CD3 cDNA fragment DNA was generated by PCR amplification, using the shuttle plasmid pLGD638 as template (pLGD638 contains a synthetic/oligonucleotide-assembled FSH beta cDNA sequence). The integrity of the construct was confirmed by sequencing and compared with the human beta subunit sequence deposited in the GenPept database (Accession Number 476441).

In brief, the pGTH-alpha and pGTD-bCD3 plasmids were linearized, repurified, and then co-transfected into adherent AV23-RGT18 cells. Following selection with medium containing 0.25 uM methotrexate and 100 µg/ml hygromycin-B, along with 200 µg/ml G418 to maintain the glutamate transporter genotype of the AV12-RGT18 cells, individual stable clones were isolated either manually or via flow-assisted cell sorting. Highest producing clones were identified by analysis of conditioned medium with a commercial FSH Elisa kit. Several clones were adapted to serum-free suspension and further amplified to obtain isolatable quantities of the FSH variant heterodimer.

Example 4

Expression In CHO-K1 Cells

A CHO-K1 cell line (LONZA Biologics plc.) was developed to produce a FSH variant heterodimer composed of the alpha subunit of SEQ ID NO:5 and the beta subunit of SEQ ID NO:11.

The expression vector cassette contains the encoding DNA for alpha subunit, SEQ ID NO:5, and the encoding DNA for the beta subunit, SEQ ID NO:11. are controlled by two different promoters: CMV for the beta subunit and EF1 Alpha for the alpha subunit. Each alph and beta subunit sequence uses the Bovine Growth Hormone polyA tail. Additionally the vector contains the Glutamine Synthetase gene, controlled by the SV40 Late Promoter and containing the SV40 polyA tail, is used as the selectable marker. This vector was used to transfect the CHO-K1 cells.

The cell line was grown in GibcoBRL's CD CHO media under selective pressure of L-methionine sulfoximine. ELISA assays were used to identify master wells expressing FSH variant. Several master wells were subjected to cloning and amplification procedures. These experiments led to the clonal cell line 2B6.1C3.25 which had suitable titers. Expression studies conducted in small scale shake flasks (20-60 ml) have shown that this line expresses FSH variant at 30 mg/L after 7 to 8 days.

Example 5

Purification of FSH Variants from CHO or AV-12 Cells

Purification of FSH variant heterodimer comprised of an alpha subunit of SEQ ID NO:5 and a beta subunit of SEQ ID:11 can be accomplished by a number of methods described and known in the art from monolayer or suspension cultures of either CHO-K1 or AV12 cell lines or other production lines suitably available. One method for isolating the disclosed FSH variant from the culture containing medium is subjecting the culture medium to cation exchange chromatography, dye affinity chromatography and gel filtration chromatography to purify the protein. In the case of suspension cultures, which may contain detergents, additional purification steps may be needed such as a Q-Sepharose step. The chromatographic steps can be further added to or optimized for pH, conductivity, buffer composition and running conditions (column dimensions, flow rates, etc). Purity and yield can be analyzed by SDS-PAGE gels (both Coomassie staining and Western blotting), ELISA assays, exclusion chromatography and protein concentration by UV absorbance at 277 nm or other known techniques.

Purification and chromatographic fractionation can be achieved by following the further details for each isolation step given below. For monolayer cultures, the conditioned medium is concentrated and diafiltered prior to application to the cation exchange column. The Q-Sepharose batching step can be included for suspension cultures to remove detergents that may be present.

1. Concentration

Typically if 0.02 to 0.04% Pluronic F68 is used for AV12 suspension cultures, whereas there is 0.1 to 0.18% in the media used for CHO suspension cultures. The conditioned medium, clarified by the cell culture group using centrifugation and filtration through a cheese cloth, is concentrated using a tangential flow filtration system ProFlux (ProFlux M12 from Millipore) with a S3YM10 spiral cartridge (Amicon #540633). Depending on the amount of Pluronic F68 that was used, the medium is concentrated 4 to 10-fold so that there is 0.2-0.4% Pluronic F68 in the concentrated medium. The final volume of material after concentration is usually 2-3 L starting from 8 L for CHO-K1 and 24 L for AV12 cultures.

2. Batching with Q-Sepharose

For each liter of starting conditioned medium before concentration, 50 ml of Fast Flow Q-Sepharose resin (Pharmacia 17-0510-01, pre-equilibrated with 20 mM Tris, pH 7.4) and sufficient NaCl to give a final conductivity of 200 mM (~20 mS/cm) are added to the concentrated medium and stirred gently overnight at 4° C.

3. Diafiltration

After overnight batching of the concentrated medium with Q-Sepharose resin, the resin is allowed to settle, the supernatant is decanted out and filtered using a CUNO system with a Zeta Plus 30-SP Filter (#B0406-30SP from Sun Source Fauver) and a Masterflex pump at a flow rate of 170 ml/min. The medium is then further concentrated to about 800 ml and diafiltered using 5-6 volumes of 20 mM Tris pH 7.4 in the Proflux system. At this point, the conductivity is ~2 mS/cm. The pH is adjusted to 5.0 with 1 N HCl and the solution is again filtered using a fresh Zeta Plus 30-SP filter in the CUNO system and immediately loaded onto the Cation Exchange column.

4. Cation Exchange Chromatography (CEX)

Column: Pharmacia SP-Sepharose Fast Flow (17-0729-01) is used to pack a 50 ml column for ~100-200 mg of FSH (total protein ~500-600 mg). Buffers are: A: 20 mM sodium phosphate, pH 5.0; and B: 20 mM sodium phosphate, pH 5.0, 1M NaCl The sample is adjusted to pH 5.0, clarified by filtration and immediately loaded onto the column and run at 5 ml/min with 4 Column Volumes before starting a gradient of 0% to 50% B over 15 Column Volumes. 3 min fractions are collected (15 ml). Fractions are collected into 400 ml of 1 M Tris, pH 8.0.

Coomassie-stained SDS PAGE gels are used to choose FSH-containing fractions to pool (typically the pool size is 200 to 250 ml for a 50 ml column). This pool is dialyzed against 20 mM Tris, pH 7.4 overnight at 4° C. to drop conductivity to <3 mS/cm.

5. Dye Affinity Chromatography (DAC)

Column: Mimetic Blue Dye 1 A6XL, 0090-0500 from Prometic Biosciences Inc. is used in a 50 ml column for ~40 mg of FSH). Buffers are: A: 25 mM phosphate, pH 6.5 (conductivity is 4.5 to 5 mS/cm); B: 25 mM phosphate, 150 mM KCl, pH 6.5; C: 25 mM phosphate, 1M KCl, pH 8.0

After dialysis of CEX pool, the pH is adjusted to 6.5, and loaded onto the DAC column at 3 ml/min. A gradient from 100%A to 50%A; 50% B is applied for 4 Column Volumes, then eluted with 100% Buffer C for 5 Column Volume, collecting Fractions of 3 min (9 ml).

Coomassie-stained SDS-PAGE gels are used to choose FSH-containing fractions to pool. Typically, the pool size is 90 to 100 ml for a 50 ml column. The pool is concentrated to 4 ml using Millipore Ultrafree centrifuge devices (UFV2BCC40, 5000 MWCO, spun at 2000 rpm) and loaded onto a Gel Filtration column.

6. Gel Filtration

Column: BioPilot Superdex 75 Prep Grade 35/600 column is used for 50 to 100 mg of FSH. Buffers are: 1×PBS (made from GIBCO 10×PBS, #70011) plus 100 mM NaCl. Final composition of the buffer is 1 mM monobasic potassium phosphate, 3 mM dibasic sodium phosphate, 253 mM sodium chloride, pH 7.4.

The column is loaded with 4 ml of FSH from DAC step in 1×PBS as described above at a flow rate: 3 ml/min collecting 1 min (3 ml) fractions.

The purity of FSH after this step is usually >95% by Coomassie and silver-stained gels.

FORMULATION/MANUFACTURE EXAMPLES

Example 6

Effect of Preservatives on Physical Stability of FSH

Since preservatives tend to denature or destabilize protein or induce aggregation (Brange, J. and Langkjar, L., Acta Pharm. Nord, 4, 149-158, 1992; Maa Y F and Hsu C, International Journal of Pharmaceutics, 140, 155-168, 1996), the physical stability of uFSH (uFSH—Vitro Diagnostics—Human Urofollitropin) in the presence of different preservatives was examined using the dynamic light scattering technique. All measurements were obtained with a system consisting of a Lexel 95 Argon Laser (488 nm), a Brookhaven Instruments model BI-200SM goniometer, and a BI9000AT autocorrelator. Data parameters consist of: initial photon counts adjusted to 100,000 counts/sec, 30 second duration, 31 dust cutoff value, and a 90° scattering angle.

Preservatives were added to a 1.5 ml solution of 1 mg/ml urinary follicle stimulatin hormone (uFSH—Vitro Diagnostics—Human Urofollitropin) which had been dialyzed against 1×PBS overnight at pH 7.4. The concentration of preservative was selected to be the concentration generally known to provide adequate anti-microbial activity. In a laminar flow hood, this sample was filtered through a 0.1 μm Anotop-Plus filter (10 mm) into a 12 mm DLS test tube. The sample was placed in the DLS holder which had been equilibrated at 37° C. The auto-correlation function was determined every 15 minutes for 24 hours and analyzed to yield the hydrodynamic parameter. This measurement demonstrated that more than 99% of the protein molecules had an average diameter of about 5.7 nm. A small population (<1%) had an average diameter of about 200 nm. The presence of the preservatives did not change the size distribution of the molecule appreciably after 24 hour at 37° C. The representative data at 24 hr. was then analyzed using NNLS (Non Negative Linear Squares) program as shown in Table I. More than 99% of the molecules were in particles with an average diameter of about 5.7 nm. Using an empirical equation relating crystallographically determined hydrodynamic radius with molecular weight (Squire, P. G. and Himmel, M. E., in Arch. Bioch. Biophys., 196, pp. 165-177, 1979) this average DLS particle size corresponds to about 36,000 daltons, which is consistent with the molecular weight of the uFSH heterodimer. The remaining small population of particles (<1%) had an average diameter of about 200 nm. These data show, in Table VI that the preservatives studied did not significantly aggregate uFSH under the conditions tested.

TABLE VI

Size distribution of uFSH in formulations containing different preservatives.

| Preservative | Preservative Concentration (mg/ml) | Small Particles (~5.7 nm) | Large Particles (~200 nm) |
|---|---|---|---|
| None | 0 | >99% | <1% |
| m-cresol | 3.5 | >99% | <1% |
| Phenol | 3.5 | >99% | <1% |
| Benzyl alcohol | 10 | >99% | <1% |
| Methylparaben | 1 | >99% | <1% |
| Chlorocresol | 2 | >99% | <1% |

Example 7

Thermal Denaturation Studies on uFSH Formulations

The thermal unfolding transition for uFSH (UFSH—Vitro Diagnostics—Human Urofollitropin) as a function of solvent conditions was monitored by differential scanning calorimetry (DSC). Experiments were carried out on a VP-DSC MicroCalorimeter (MicroCal inc., Northampton, Mass.; Plotnik, V. V., et. al., Anal. Biochem., 250:237-244, 1997) using VPViewer software for data acquisition and Origin DSC software for data analysis. The matched sample cell and reference cell were lollipop-shaped, fabricated from tantalum, with a working volume of 0.5 ml. Approximately 1 mg/ml uFSH samples were dialyzed against appropriate buffer overnight and concentration of the protein in the sample was determined by UV spectroscopy. The proteins were then diluted to 0.4-0.5 mg/ml for the DSC experiments. The dialysate was used as reference solution. Sample and reference solutions were degassed for 5 minutes before loading into the cells with a 2.5 ml needle through a filling funnel. Pressure was kept at about 30 psi with the pressure cap. For all measurements in this study, the instrument was run overnight with buffers in both the reference cell and sample cell to establish thermal history prior to sample runs. The data was analyzed with Origin DSC software using a two-state model (Sturtevant, J. M., Annu. Rev. Phys. Chem., 38:463-488, 1987). The midpoint of the transition temperature ($T_m$) at different solution conditions is summarized in Table VII. The protein undergoes a very cooperative transition with a $T_m$ of 77.3° C. in PBS buffer at pH 7.4. Thermal denaturation is irreversible on the time scale of the measurements as shown by the absence of transition in the second scan immediately following the first scan. However, the dissociated subunits stay as monomers in solution and these monomers can then reassociate to form biologically active dimer in the course of the days (data not shown). The effects of the addition of preservatives, m-cresol, phenol, benzyl alcohol, methylparaben, and chlorocresol at the concentrations specified below shows only marginal effect on the $T_m$ as demonstrated in Tables VII.

TABLE VII

Effect of pH, salt, and preservatives on $T_m$ of uFSH in solution as monitored by DSC.

| Solution conditions | $T_m$ (° C.) |
|---|---|
| PB (9.5 mM phosphate) | |
| pH 5.7 | 72.4 |
| pH 6.6 | 74.3 |
| pH 7.6 | 74.8 |
| pH 8.6 | 75.3 |
| 100 mM NaCl, pH 7.6 | 76.1 |
| PBS at pH 7.4 | 77.3 |
| 3.5 mg/ml m-Cresol | 75.3 |
| 3.5 mg/ml Phenol | 75.0 |
| 10 mg/ml Benzyl Alcohol | 73.5 |
| 1 mg/ml Methyl Paraben | 76.1 |
| 2 mg/ml Chlorocresol | 74.6 |

Example 8

Stability of UFSH as a Function of pH

Stability of UFSH (UFSH—Vitro Diagnostics—Human Urofollitropin) in PBS was determined for various pHs. Percent of heterodimer as a function of pH was monitored by size exclusion chromatography (SEC) in Table VIII.

TABLE VIII

Percent of heterodimer as a function of pH as monitored by SEC.

| pH | Percent Dimer |
|---|---|
| 7.0 | 95.0 |
| 6.5 | 95.0 |
| 6.0 | 95.0 |
| 5.5 | 95.0 |
| 5.0 | 95.0 |
| 4.5 | 95.0 |
| 4.0 | 95.0 |
| 3.5 | 95.0 |
| 3.25 | 87.7 |
| 3.0 | 62.3 |
| 2.5 | 17.6 |
| 2.0 | 5.0 |

Example 9

Stability of uFSH Preserved and Non-Preserved Formulations

A solution of uFSH (uFSH—Vitro Diagnostics—Human Urofollitropin) was prepared in PBS (Dulbecco's, GIBCO) and further diluted with PBS to a concentration of about 50 μg/ml. The protein concentration was determined on a Hewlett Packard Model 8452A Diode Array Spectrophotometer.

A portion of the uFSH solution was added to a beaker containing a pre-weighed sample of m-cresol to give a final m-cresol concentration of about 3.16 mg/ml. 1-ml aliquots of the preserved and non-preserved solution were placed in plastic centrifuge tubes and incubated up to 238 days at about 22° C., 37° C. and 45° C. At various times, aliquots were injected onto a Superdex-75 HR 10/30 column (Pharmacia) equilibrated and run at ambient temperature at 0.5 ml/min. in PBS. The eluant was monitored at 214 nm. The percentage of the heterodimer was calculated from the ratio of the area of dimer peak divided by the total area of dimer peak and monomer peaks, as shown in Table III. After 64 days, about 79% of the uFSH molecules in solution with m-cresol remain as intact dimer at 37° C. and more than 52% stay as dimer at 45° C. Surprisingly, after 63 days at room temperature, there is minimal dissociation of uFSH heterodimer in both the non-preserved and preserved solutions. It is remarkable that at 23° C., 37° C., and 45° C. there is generally relatively low dissociation of uFSH heterodimer in both non-preserved and preserved solutions at days 4, 8, 16, 21, 28, 29, 43, 63, 64, 126, 127, 237, and 238.

TABLE IX

Percent Dimer in Preserved and Non-preserved uFSH solutions.

| | PBS | | | PBS + m-cresol | | |
|---|---|---|---|---|---|---|
| Days | 23° C. | 37° C. | 45° C. | 23° C. | 37° C. | 45° C. |
| 0 | 96.0 | 96.0 | 96.0 | 93.8 | 93.8 | 93.8 |
| 4 | — | 93.0 | 91.7 | — | 91.8 | 85.6 |
| 8 | 94.3 | 92.7 | 89.5 | 93.6 | 88.9 | 80.0 |
| 16 | 94.1 | 91.1 | 84.3 | 92.5 | 87.0 | 73.8 |
| 21 | 94.0 | 91.0 | 83.1 | — | — | — |
| 22 | — | — | — | 92.3 | 84.7 | 68.8 |
| 28 | 92.8 | 89.8 | — | 92.7 | 83.7 | — |
| 29 | — | — | 79.9 | — | — | 65.3 |
| 43 | 93.3 | 89.5 | 75.9 | 91.6 | 81.5 | 59.2 |
| 63 | 92.9 | — | — | 92.6 | — | — |
| 64 | — | 88.2 | 68.6 | — | 78.9 | 52.5 |
| 126 | 91.5 | 85.5 | — | 89.6 | 71.2 | — |
| 127 | — | — | 58.2 | — | — | 43.8 |
| 237 | 92.3 | 83.1 | — | 91 | 62.0 | — |
| 238 | — | — | 57.9 | — | — | 39.5 |

Example 10

Bioactivity Measurements of UFSH Samples

HEK 293 cells stably transfected with a cAMP sensitive b-lactamase (BLAM) reporter vector (Zlokarnik, et al., 1998, *Science* 279:84-88) were transfected with a human FSH receptor expression vector encoding a hygromycin selectable marker and incubated in hygromycin for 3 weeks. The surviving cells were treated with 10 µg/ml of FSH (Sigma) for 5 hours and the population of FSH activated cells showing the highest intensity of blue fluorescence were identified and isolated by FACS. This polyclonal population was expanded, treated with 10 µg/ml of FSH for 5 hours, and FACS sorted into single cell clones. Two clonal cell lines were analyzed by the BLAM microtiter plate assay and showed a 6 to 8 fold increase in blue/green ratio. The FSH-R cell line with the greatest fold increase in BLAM expression was chosen as the cell line to be used in the subsequent FSH assays.

The FSH receptor cell line harboring the cAMP sensitive BLAM reporter was seeded in 100 µl Growth Medium (DMEM catalog number 11965-092, 10% FBS, 500 µg/ml Gentamicin) at 20,000 cells/well in a poly-D-lysine coated, 96-well black wall tissue culture plate, and incubated overnight at 37° C. under 5% $CO_2$. The Growth Medium was replaced by 100 µl Assay Medium (DMEM catalog number 11965-092, 0.5% FBS, 500 µg/ml Gentamicin) and the plate was incubated overnight at 37° C. and 5% CO2. The Assay Medium was removed and 100 µl of Assay Medium containing the indicated concentration of the FSH was then added to each well and the plate was incubated for 5 hours at 37° C. under 5% $CO_2$. 20 µl of the BLAM substrate loading, composed of 6 µl of 1 mM CCF2-AM in DMSO, 6 µl Pluronic Acid (100 µg/ml in 0.1% acetic acid DMSO) into 1 ml 2% PEG-400 and 10% ESS (Aurora Biosciences) was then added into each well. After 1 hour of incubation at room temperature, the ratio of blue (395 nm excitation/460 nm emission) to green (395 nm excitation/530 nm emission) fluorescence intensities was determined with a Cytofluor (Perseptives Biosystems, Series 4000 multi-well plate reader). The fold increase in blue/green ratio resulting from the presence of FSH was calculated by dividing each ratio by the blue/green ratio of the control sample.

A solution of urinary FSH (uFSH—Vitro Diagnostics—Human Urofollitropin)at 50 µg/ml in PBS (Sample A) was prepared as in Example 9. A portion of this solution was heated at 90° C. for 10 minutes to dissociate more than 99% of the heterodimer into the two monomers (as shown by SEC analysis) and was used in this assay (Sample B) as a negative control. Another portion of the FSH solution was modified to include about 3.15 mg/ml of m-cresol (Sample C). The bioactivity of these three test samples was evaluated in the FSH-R 293-Cre-BLAM assay on two separate plates. The average of triplicate analyses on each plate is shown in Table X. This data shows the assay was performing very reproducibly. It also showed that the dissociated heterodimer lost bioactivity (Sample B) and that the FSH in the formulation containing the m-cresol (Sample C) retained full bioactivity.

TABLE X

Blue/Green fold increase in the FSH receptor bioactivity assay.

| Test Sample Concentration (nM) | Sample A Plate 1 | Sample A Plate 2 | Sample B Plate 1 | Sample B Plate 2 | Sample C Plate 1 | Sample C Plate 2 |
|---|---|---|---|---|---|---|
| 0 (control) | 1.00 | 1.00 | 1.00 | 1.00 | 1.00 | 1.00 |
| 0.003 | 1.68 | 1.67 | 1.07 | 1.06 | 1.22 | 1.22 |
| 0.01 | 1.91 | 1.86 | 1.06 | 1.06 | 1.58 | 1.62 |
| 0.03 | 3.00 | 2.89 | 1.06 | 1.06 | 2.72 | 3.21 |
| 0.1 | 4.00 | 4.09 | 1.18 | 1.18 | 3.86 | 3.85 |
| 0.3 | 4.53 | 4.47 | 1.24 | 1.24 | 4.61 | 4.63 |
| 1 | 4.88 | 4.71 | 1.68 | 1.69 | 4.81 | 4.77 |
| 3 | 4.60 | 4.64 | 2.61 | 2.58 | 4.83 | 4.92 |

Example 11

Bioactivity Measurements of Preserved and Non-Preserved uFSH Samples

Bioactivity measurements of urinary FSH(uFSH—Vitro Diagnostics—Human Urofollitropin) samples were determined in the in vitro bioactivity assay as described in Example 10. In vitro assay results of two samples uFSH in PBS at 23° C., PBS with and without m-cresol at 23° C. after 11 month compared to a control in table XI. The data indicates that preserved and non-preserved uFSH samples maintain full biological activity after 11 months in this assay.

TABLE XI

In vitro bioactivity of preserved and non-
preserved uFSH solution after 11 month at 23° C.

| Sample | Relative potency |
|---|---|
| uFSH control (50 μg/ml, PBS, fresh) | 1.0 |
| uFSH (50 μg/ml, PBS, 23° C. for 11 months) | 1.27 |
| uFSH (50 μg/ml, PBS, 3.15 mg/ml m-cresol, 23° C. for 11 months) | 0.86 |

Example 12

Cartridge Compatibility of Preserved and Non-Preserved rFSH Variant

To test the compatibility of formulated rFSH variant (alpha subunit SEQ ID NO:5; beta subunit SEQ ID NO:11) solutions with cartridges, 4-ml solutions of the samples as listed in Table 12 were prepared from stock solutions listed below:
1.85 mg/ml rFSH variant in PBS
1.73 mg/ml rFSH variant in PB
20 mg/ml m-cresol in PBS
20 mg/ml m-cresol in PB.
20% glycerol in PB
1×PBS After mixing, 1.7 ml of each solution was pipetted into individual cartridges with minimal head-space allowed. Two cartridges were filled for each sample. Caps were sealed on the cartridges. The cartridges were then incubated at 30° C. for 20 days. After filling, the remainder of the samples were incubated at 40° C. to serve as control samples. In vitro activity of these samples was measured after 20 days of incubation at 30° C., using the method described in Example 11. The activity of these samples was compared to corresponding control samples at zero time point. As shown in Table XII below, rFSH sample at 50 μg/ml in PBS and sample at 200 μg/ml in PBS and 3.15 mg/ml m-cresol are stable in cartridges (cartridge 1 and cartridge 4). These samples remain fully active after 20 days of incubation at 30° C. However, samples in phosphate buffer without NaCl were less potent under these conditions. The activity of rFSH samples in phosphate buffer and 1.6 e glycerol decreases in comparison to that of control (cartridge 2 and cartridge 3)

TABLE XII

In vitro activity of preserved and non-preserved
samples incubated at 30° C. for 20 days in cartridges.

| Sample | Sample Conditions | Relative Potency |
|---|---|---|
| Cartridge 1 | 200 μg/ml rFSH variant, 3.15 mg/ml m-cresol, PBS, pH 7.4 | 1.06 |
| Cartridge 2 | 200 μg/ml rFSH variant, 1.6% glycerol, PB, pH 7.4 | 0.81 |
| Cartridge 3 | 50 μg/ml rFSH variant, 1.6% glycerol, 3.15 mg/ml m-cresol, PB, pH 7.4 | 0.60 |
| Cartridge 4 | 50 μg/ml rFSH variant, PBS, pH 7.4 | 1.10 |

As demonstrated by these examples, following the methods and techniques described one can generate surprisingly stable composition and formulations of FSH or a FSH variant. These compositions and formulations result in the development of the presently claimed articles of manufacture. Since about 1970, the courts have held that printed information in an article of manufacture does not remove the article from the realm of patentabililty so long as the item and the invention as a whole satisfy the other requirements of the statute, such as novelty and nonobviousness. Since the FSH or a FSH variant products taught in the prior art expressly teach that such solutions are suitable only for immediate use and after use the contents must be disposed of, rather than the presently claimed product suitable for use 24 hours or greater, the article of manufacture embodies new and non-obvious invention that is distinct and different from the prior art.

The principles, preferred embodiments, and modes of operation of the present invention have been described in the foregoing specification. The invention intended to be protected herein, however, is not to be construed as limited to the particular forms disclosed, since they are to be regarded as illustrative rather than restrictive. Variations and changes may be made by those skilled in the art without departing from the spirit of the invention.

Example 9

Formulation Stability of Preserved and Non-Preserved FSH Variant Samples

A stock solution of recombinant FSH variant (alpha subunit is SEQ ID:5; beta subunit SEQ ID:11) at about 1 mg/ml in phosphate buffered saline (PBS, Dulbecco's, GIBCO) was diluted to 50 μg/ml or 20 μg/ml with either PBS or PBS containing m-cresol to give a final m-cresol concentration of 3.15 mg/ml. Similarly, another set of samples was made using 10 mg/ml benzyl alcohol as preservative. 1-ml aliquots of the preserved and non-preserved solution were incubated at 4, 22, 37° C. for up to three months in plastic eppendorf tubes. At various times, aliquots were injected onto a Superdex 75 gel filtration column (Pharmacia) equilibrated with PBS and run at ambient temperature with a flow rate of 0.07 ml/min and the run time of 35 minutes. Detection was monitored by UV absorbance at 214 nm over time. Peak areas were integrated, and the percentage of the heterodimer was calculated as a ratio of area of heterodimer peak over the total area of the dimer and monomer peaks.

As shown in Table IX, there is minimal dissociation of the heterodimer under various solution conditions after three month of incubation at room temperature or below. Greater than 50% heterodimer remains intact after three month incubation at 37° C. The stability of heterodimer is higher with more concentrated solution.

TABLE IX

Heterodimer stability of rFSH variant monitored by SE-HPLC.

| | % Dimer | | | | | |
|---|---|---|---|---|---|---|
| | 1 month | | | 3 months | | |
| Sample | 4° C. | 22° C. | 37° C. | 4° C. | 22° C. | 37° C. |
| 20 μg/ml in PBS | 100 | 100 | 88.9 | 100 | 100 | 77.3 |
| 20 μg/ml in PBS 3.15 mg/ml m-cresol | 100 | 100 | 86.2 | 100 | 100 | 64.6 |
| 20 μg/ml in PBS 10 mg/ml benzyl alcohol | 100 | 100 | 89.1 | 100 | 100 | 57.1 |
| 50 μg/ml in PBS | 100 | 100 | 100 | 100 | 100 | 81.1 |
| 50 μg/ml in PBS 3.15 mg/ml m-cresol | 100 | 100 | 90 | 100 | 100 | 75.7 |
| 50 μg/ml in PBS 10 mg/ml benzyl alcohol | 100 | 100 | 87 | 100 | 100 | 61.0 |

We claim:

1. A method for providing a stable, liquid, multi-use human FSH formulation comprising:

preparing an aqueous pharmaceutical formulation comprising human FSH and a preservative selected from the group consisting of benzyl alcohol, m-cresol and mixtures thereof, the human FSH consisting of an α-subunit having SEQ ID NO:5 and a β-subunit having SEQ ID NO:6 held together by noncovalent interactions, the human FSH being present as the biologically-active, heterodimeric protein form of human FSH at a concentration of about 5.0 µg/mL to about 200 µg/mL, the preservative being present in an amount effective to yield anti-microbial effect for the formulation; and placing the formulation into a vial, the formulation having a stability such that it contains a pharmaceutically-effective mount of FSH after being held in the vial for a period of twenty four hours or greater.

2. The method of claim 1 and which farther includes storing the vial and included formulation at 2-40 degrees C. for a period of time exceeding 2 months, the formulation containing a pharmaceutically-effective amount of FSH after being stored in the vial at 2-40 degrees C. for a period of time exceeding 2 months.

3. The method of claim 1 which comprises placing in the vial an amount of pharmaceutical formulation sufficient for administering to a patient multiple doses of a pharmaceutically-effective amount of human FSH, the formulation in the vial having a stability such that each of the multiple doses inch des a pharmaceutically-effective amount of FSH when administered over a period of twenty four hours or greater.

4. The method of claim 3 in which the amount is sufficient for administering a pharmaceutically-effective amount of human FSH over 96 hours or greater, the formulation in the vial having a stability such that the formulation includes a pharmaceutically-effective amount of FSH for 96 hours or greater.

5. The method of claim 4 in which the amount is sufficient for administering a cycle of treatment to a patient, the formulation in the vial having a stability such that the formulation in eludes a pharmaceutically-effective amount of FSH for administering over a cycle of treatment for a patient.

6. The method of claim 1 which comprises placing the formulation into a pen-injector system, the formulation retaining biological activity after being stored in the pen-injector system at 2-40 degrees C. for a period of time exceeding 2 months.

7. The method of claim 1 in which the preservative is benzyl alcohol.

8. The method of claim 1 in which the preservative is m-cresol.

9. The method of claim 1 in which the formulation has a stability such that the size distribution of the FSH molecules does not change appreciably after 24 hours at 37° C.

10. The method of claim 1 in which the formulation has a stability such that greater than 50% heterodimer remains intact after three months at 37° C.

11. A method for preparing a stable, liquid, reconstituted, multi-use, human FSH formulation comprising:

providing a lyophilized mixture of human FSH;

providing an aqueous diluent containing a preservative selected from the group consisting of benzyl alcohol, m-cresol and mixtures thereof;

reconstituting the mixture with the diluent such that the resulting formulation contains human FSH consisting of an α-subunit having SEQ ID NO:5 and a β-subunit having SEQ ID NO:6 held together by noncovalent interactions, the human FSH in the reconstituted mixture being present as the biologically-active, heterodimeric protein form of human FSH at a concentration of about 5.0 μg/mL to about 200 μg/mL, and an effective anti-microbial amount of the preservative, the resulting formulation having a stability such that it contains a pharmaceutically-effective amount of FSH after being held for a period of twenty four hours or greater.

12. The method of claim 11 in which the preservative is benzyl alcohol.

13. The method of claim 11 in which the preservative is m-cresol.

14. The method of claim 11 in which the formulation retains biological activity after being stored in the vial at 2-40 degrees C. for a period of time exceeding 2 months.

15. The method of claim 11 in which the formulation is in an amount sufficient for administering a cycle of treatment to a patient, the formulation having a stability such that the formulation includes a pharmaceutically-effective amount of FSH for administering over a cycle of treatment for a patient.

16. The method of claim 11 and which farther includes holding the resulting formulation for a period of twenty four hours or greater, the formulation containing a pharmaceutically-effective amount of FSH after having been held for twenty four hours or greater.

17. A stable, liquid, multi-use, pharmaceutical formulation, comprising:

an aqueous diluent;

a preservative selected from the group consisting of benzyl alcohol, m-cresol and mixtures thereof; and human FSH;

said human FSH being present in said pharmaceutical formulation in a solubilized biologically-active heterodimeric protein form consisting of an alpha-subunit having SEQ ID NO:5 and a beta-subunit having SEQ ID NO:6, the alpha-subunit and beta-subunit held together by noncovalent interactions;

said human FSH being present in the biologically-active, heterodimeric protein form at a concentration of about 5.0 μg/ml to about 200 μg/ml;

said preservative being present in said pharmaceutical formulation in an effective anti-microbial amount;

the formulation having a Stability such that it contains pharmaceutically-effective amount of FSH after being held for a period of twenty four hours or greater.

18. The pharmaceutical formulation of claim 17, wherein said human FSH present in said pharmaceutical formulation is in sufficient amount to administer multiple instances of an effective dose of the human FSH for ovarian follicle or testicular stimulation in a human.

19. A pharmaceutical product suitable for use in administering human FSH to a patient over a period of twenty four hours or greater, comprising:

a single vial containing the pharmaceutical composition of claim 17, wherein said human FSH is present in said single vial in sufficient amount to administer multiple instances of an effective dose of the human FSH for ovarian follicle or testicular stimulation in a human.

20. The pharmaceutical product of claim 19 in which the preservative is benzyl alcohol.

21. The pharmaceutical product of claim 19 in which the preservative is m-cresol.

22. The pharmaceutical product of claim 19 in which the formulation retains biological activity after being stored in the vial at 2-40 degrees C. for a period of time exceeding 2 months.

23. The pharmaceutical product of claim 19 in which the single vial contains an amount of formulation sufficient for administering a cycle of treatment to a patient, the formulation having a stability such that the formulation includes a pharmaceutically-effective amount of FSH for administering over a cycle of treatment for a patient.

24. The pharmaceutical formulation of claim 17 in which the human FSH is recombinant human FSH.

25. The pharmaceutical product of claim 24 in which the preservative is benzyl alcohol.

26. The pharmaceutical product of claim 24 in which the preservative is m-cresol.

27. The pharmaceutical formulation of claim 17 in which the human FSH is substantially pure.

28. The formulation of claim 17 in which the preservative is benzyl alcohol.

29. The formulation of claim 17 in which the preservative is m-cresol.

30. The formulation of claim 17 in which the formulation retains biological activity after being stored in the vial at 2-40 degrees C. for a period of time exceeding 2 months.

31. The formulation of claim 17 in which the formulation is in an amount sufficient for administering a cycle of treatment to a patient, the formulation having a stability such that the formulation includes a pharmaceutically-effective amount of FSH for administering over a cycle of treatment for a patient.

32. A method for providing a stable, liquid, multi-use human FSH formulation comprising:

preparing an aqueous pharmaceutical formulation comprising human FSH and a preservative selected from the group consisting of benzyl alcohol, m-cresol and mixtures thereof, the human FSH consisting of an α-subunit having SEQ ID NO:5 and a β-subunit having SEQ ID NO:6 held together by noncovalent interactions, the human FSH being present as the biologically-active, heterodimeric protein form of human FSH at a concentration of about 5.0 μg/mL to 2 mg/mL, the preservative being present in an amount effective to yield an anti-microbial effect for the formulation;

placing the formulation into a vial; and storing the vial and the included formulation at 2-40 degrees C. for a period of time exceeding 2 months, the formulation included a pharmaceutically-effective amount of FSH after being stored at 2-40 degrees C. for a period of time exceeding 2 months.

* * * * *

UNITED STATES PATENT AND TRADEMARK OFFICE
CERTIFICATE OF CORRECTION

PATENT NO.         : 7,446,090 B2
APPLICATION NO. : 11/482569
DATED              : November 4, 2008
INVENTOR(S)        : James Arthur Hoffman It is certified that error appears in the above-identified patent and that said Letters Patent is hereby corrected as shown below:

Column 51, line 51, change "farther" to --further--.
Column 51, line 62, change "inch des" to --includes--.
Column 52, lines 38-39, change "in eludes" to --includes--.
Column 53, line 20, change "farther" to --further--.

Signed and Sealed this

Twenty-third Day of December, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,446,090 B2 |
| APPLICATION NO. | : 11/482569 |
| DATED | : November 4, 2008 |
| INVENTOR(S) | : James Arthur Hoffmann |

Page 1 of 1

It is certified that error appears in the above-identified patent and that said Letters Patent is hereby corrected as shown below:

Title Page, Item (63) under "Related U.S. Application Data" please replace the first paragraph with the following paragraph:

--Continuation of application No. 09/928,198 filed on Aug. 10, 2001, now abandoned, which is a division of application No. 09/744,431 filed Jan. 22, 2001, now abandoned, which is a national stage of PCT/US99/16031 filed on Jul. 15, 1999.--

Signed and Sealed this

First Day of September, 2009

David J. Kappos
*Director of the United States Patent and Trademark Office*

SEQUENCE LISTING

<160> NUMBER OF SEQ ID NOS: 20

<210> SEQ ID NO 1
<211> LENGTH: 96
<212> TYPE: PRT
<213> ORGANISM: mammalian

<400> SEQUENCE: 1

Phe Pro Asp Gly Glu Phe Thr Met Gln Gly Cys Pro Glu Cys Lys Leu
 1               5                  10                  15

Lys Glu Asn Lys Tyr Phe Ser Lys Pro Asp Ala Pro Ile Tyr Gln Cys
                20                  25                  30

Met Gly Cys Cys Phe Ser Arg Ala Tyr Pro Thr Pro Ala Arg Ser Lys
            35                  40                  45

Lys Thr Met Leu Val Pro Lys Asn Ile Thr Ser Glu Ala Thr Cys Cys
        50                  55                  60

Val Ala Lys Ala Phe Thr Lys Ala Thr Val Met Gly Asn Val Arg Val
65                  70                  75                  80

Glu Asn His Thr Glu Cys His Cys Ser Thr Cys Tyr Tyr His Lys Ser
                85                  90                  95

<210> SEQ ID NO 2
<211> LENGTH: 111
<212> TYPE: PRT
<213> ORGANISM: mammalian

<400> SEQUENCE: 2

Arg Ser Cys Glu Leu Thr Asn Ile Thr Ile Thr Val Glu Lys Glu Glu
 1               5                  10                  15

Cys Gly Phe Cys Ile Ser Ile Asn Thr Thr Trp Cys Ala Gly Tyr Cys
                20                  25                  30

Tyr Thr Arg Asp Leu Val Tyr Arg Asp Pro Ala Arg Pro Asn Ile Gln
            35                  40                  45

Lys Thr Cys Thr Phe Lys Glu Leu Val Tyr Glu Thr Val Lys Val Pro
        50                  55                  60

Gly Cys Ala His His Ala Asp Ser Leu Tyr Thr Tyr Pro Val Ala Thr
65                  70                  75                  80

Glu Cys His Cys Ser Lys Cys Asp Ser Asp Ser Thr Asp Cys Thr Val
                85                  90                  95

Arg Gly Leu Gly Pro Ser Tyr Cys Ser Phe Arg Glu Ile Lys Glu
            100                 105                 110

<210> SEQ ID NO 3
<211> LENGTH: 96
<212> TYPE: PRT
<213> ORGANISM: mammalian

<400> SEQUENCE: 3

Phe Pro Asp Gly Glu Phe Thr Thr Gln Asp Cys Pro Glu Cys Lys Leu
 1               5                  10                  15

Arg Glu Asn Lys Tyr Phe Phe Lys Leu Gly Val Pro Ile Tyr Gln Cys
                20                  25                  30

Lys Gly Cys Cys Phe Ser Arg Ala Tyr Pro Thr Pro Ala Arg Ser Arg
            35                  40                  45

Lys Thr Met Leu Val Pro Lys Asn Ile Thr Ser Glu Ser Thr Cys Cys
        50                  55                  60

Val Ala Lys Ala Phe Ile Arg Val Thr Val Met Gly Asn Ile Lys Leu
65                  70                  75                  80

Glu Asn His Thr Gln Cys Tyr Cys Ser Thr Cys Tyr His His Lys Ile
            85                  90                  95

<210> SEQ ID NO 4
<211> LENGTH: 111
<212> TYPE: PRT
<213> ORGANISM: mammalian

<400> SEQUENCE: 4

Asn Ser Cys Glu Leu Thr Asn Ile Thr Ile Ala Val Glu Lys Glu Gly
1               5                   10                  15

Cys Gly Phe Cys Ile Thr Ile Asn Thr Thr Trp Cys Ala Gly Tyr Cys
            20                  25                  30

Tyr Thr Arg Asp Leu Val Tyr Lys Asp Pro Ala Arg Pro Asn Ile Gln
        35                  40                  45

Lys Thr Cys Thr Phe Lys Glu Leu Val Tyr Glu Thr Val Lys Val Pro
    50                  55                  60

Gly Cys Ala His His Ala Asp Ser Leu Tyr Thr Tyr Pro Val Ala Thr
65                  70                  75                  80

Ala Cys His Cys Gly Lys Cys Asn Ser Asp Ser Thr Asp Cys Thr Val
            85                  90                  95

Arg Gly Leu Gly Pro Ser Tyr Cys Ser Phe Gly Asp Met Lys Glu
        100                 105                 110

<210> SEQ ID NO 5
<211> LENGTH: 92
<212> TYPE: PRT
<213> ORGANISM: Homo sapiens

<400> SEQUENCE: 5

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
            85                  90

<210> SEQ ID NO 6
<211> LENGTH: 111
<212> TYPE: PRT
<213> ORGANISM: Homo sapiens

<400> SEQUENCE: 6

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro

```
                50                    55                    60
Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
                100                 105                 110

<210> SEQ ID NO 7
<211> LENGTH: 96
<212> TYPE: PRT
<213> ORGANISM: mammalian

<400> SEQUENCE: 7

Phe Pro Asp Gly Glu Phe Thr Met Gln Gly Cys Pro Glu Cys Lys Leu
 1               5                   10                  15

Lys Glu Asn Lys Tyr Phe Ser Lys Leu Gly Ala Pro Ile Tyr Gln Cys
                20                  25                  30

Met Gly Cys Cys Phe Ser Arg Ala Tyr Pro Thr Pro Ala Arg Ser Lys
             35                  40                  45

Lys Thr Met Leu Val Pro Lys Asn Ile Thr Ser Glu Ala Thr Cys Cys
 50                  55                  60

Val Ala Lys Ala Phe Thr Lys Ala Thr Val Met Gly Asn Ala Arg Val
 65                  70                  75                  80

Glu Asn His Thr Glu Cys His Cys Ser Thr Cys Tyr Tyr His Lys Ser
                85                  90                  95

<210> SEQ ID NO 8
<211> LENGTH: 111
<212> TYPE: PRT
<213> ORGANISM: mammalian

<400> SEQUENCE: 8

Asn Ser Cys Glu Leu Thr Asn Ile Thr Ile Thr Val Glu Lys Glu Glu
 1               5                   10                  15

Cys Asn Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Asn Ile Gln
             35                  40                  45

Lys Thr Cys Thr Phe Lys Glu Leu Val Tyr Glu Thr Val Lys Val Pro
 50                  55                  60

Gly Cys Ala His His Ala Asp Ser Leu Tyr Thr Tyr Pro Val Ala Thr
 65                  70                  75                  80

Glu Cys His Cys Gly Lys Cys Asp Ser Asp Ser Thr Asp Cys Thr Val
                85                  90                  95

Arg Gly Leu Gly Pro Ser Tyr Cys Ser Phe Ser Glu Met Lys Glu
                100                 105                 110

<210> SEQ ID NO 9
<211> LENGTH: 96
<212> TYPE: PRT
<213> ORGANISM: mammalian

<400> SEQUENCE: 9

Phe Pro Asp Gly Glu Phe Thr Met Gln Gly Cys Pro Glu Cys Lys Leu
 1               5                   10                  15

Lys Glu Asn Lys Tyr Phe Ser Lys Pro Asp Ala Pro Ile Tyr Gln Cys
                20                  25                  30
```

```
Met Gly Cys Cys Phe Ser Arg Ala Tyr Pro Thr Pro Ala Arg Ser Lys
            35                  40                  45

Lys Thr Met Leu Val Pro Lys Asn Ile Thr Ser Glu Ala Thr Cys Cys
 50                  55                  60

Val Ala Lys Ala Phe Thr Lys Ala Thr Val Met Gly Asn Val Arg Val
 65                  70                  75                  80

Glu Asn His Thr Glu Cys His Cys Ser Thr Cys Tyr Tyr His Lys Ser
                85                  90                  95

<210> SEQ ID NO 10
<211> LENGTH: 111
<212> TYPE: PRT
<213> ORGANISM: mammalian

<400> SEQUENCE: 10

Arg Ser Cys Glu Leu Thr Asn Ile Thr Ile Thr Val Glu Lys Glu Glu
 1               5                  10                  15

Cys Ser Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Asn Ile Gln
            35                  40                  45

Lys Ala Cys Thr Phe Lys Glu Leu Val Tyr Glu Thr Val Lys Val Pro
 50                  55                  60

Gly Cys Ala His His Ala Asp Ser Leu Tyr Thr Tyr Pro Val Ala Thr
 65                  70                  75                  80

Glu Cys His Cys Gly Lys Cys Asp Arg Asp Ser Thr Asp Cys Thr Val
                85                  90                  95

Arg Gly Leu Gly Pro Ser Tyr Cys Ser Phe Ser Asp Ile Arg Glu
            100                 105                 110

<210> SEQ ID NO 11
<211> LENGTH: 108
<212> TYPE: PRT
<213> ORGANISM: Homo sapiens

<400> SEQUENCE: 11

Asn Ser Cys Glu Leu Thr Asn Ile Thr Ile Ala Ile Glu Lys Glu Glu
 1               5                  10                  15

Cys Arg Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu
            100                 105

<210> SEQ ID NO 12
<211> LENGTH: 109
<212> TYPE: PRT
<213> ORGANISM: Homo sapiens

<400> SEQUENCE: 12
```

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met
            100                 105

<210> SEQ ID NO 13
<211> LENGTH: 110
<212> TYPE: PRT
<213> ORGANISM: Homo sapiens

<400> SEQUENCE: 13

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys
            100                 105                 110

<210> SEQ ID NO 14
<211> LENGTH: 276
<212> TYPE: DNA
<213> ORGANISM: Homo sapiens

<400> SEQUENCE: 14
gctcctgatg tgcaggattg cccagaatgc acgctacagg aaaacccatt cttctcccag    60
ccgggtgccc caatacttca gtgcatgggc tgctgcttct ctagagcata tcccactcca   120
ctaaggtcca agaagacgat gttggtccaa aagaacgtca cctcagagtc cacttgctgt   180
gtagctaaat catataacag ggtcacagta atgggggtt tcaaagtgga gaaccacacg   240
gcgtgccact gcagtacttg ttattatcac aaatct                              276

<210> SEQ ID NO 15
<211> LENGTH: 324
<212> TYPE: DNA
<213> ORGANISM: Homo sapiens

<400> SEQUENCE: 15
aatagctgtg agctgaccaa catcaccatt gcaatagaga agaagaatg tcgtttctgc     60 ataagcatca acaccacttg gtgtgctggc tactgctaca ccagggatct ggtgtataag   120

```
gacccagcca ggcccaaaat ccagaaaaca tgtaccttca aggaactggt atatgaaaca      180
gtgagagtgc ccggctgtgc tcaccatgca gattccttgt atatacaccc agtggccacc      240
cagtgtcact gtggcaagtg tgacagcgac agcactgatt gtactgtgcg aggcctgggg      300
cccagctact gctcctttgg tgaa                                             324
```

<210> SEQ ID NO 16
<211> LENGTH: 327
<212> TYPE: DNA
<213> ORGANISM: Homo sapiens

<400> SEQUENCE: 16

```
aatagctgtg agctgaccaa catcaccatt gcaatagaga aagaagaatg tcgtttctgc       60
ataagcatca acaccacttg gtgtgctggc tactgctaca ccagggatct ggtgtataag      120
gacccagcca ggcccaaaat ccagaaaaca tgtaccttca aggaactggt atatgaaaca      180
gtgagagtgc ccggctgtgc tcaccatgca gattccttgt atacataccc agtggccacc      240
cagtgtcact gtggcaagtg tgacagcgac agcactgatt gtactgtgcg aggcctgggg      300
cccagctact gctcctttgg tgaaatg                                          327
```

<210> SEQ ID NO 17
<211> LENGTH: 330
<212> TYPE: DNA
<213> ORGANISM: Homo sapiens

<400> SEQUENCE: 17

```
aatagctgtg agctgaccaa catcaccatt gcaatagaga aagaagaatg tcgtttctgc       60
ataagcatca acaccacttg gtgtgctggc tactgctaca ccagggatct ggtgtataag      120
gacccagcca ggcccaaaat ccagaaaaca tgtaccttca aggaactggt atatgaaaca      180
gtgagagtgc ccggctgtgc tcaccatgca gattccttgt atacataccc agtggccacc      240
cagtgtcact gtggcaagtg tgacagcgac agcactgatt gtactgtgcg aggcctgggg      300
cccagctact gctcctttgg tgaaatgaaa                                       330
```

<210> SEQ ID NO 18
<211> LENGTH: 333
<212> TYPE: DNA
<213> ORGANISM: Homo sapiens

<400> SEQUENCE: 18

```
aatagctgtg agctgaccaa catcaccatt gcaatagaga aagaagaatg tcgtttctgc       60
ataagcatca acaccacttg gtgtgctggc tactgctaca ccagggatct ggtgtataag      120
gacccagcca ggcccaaaat ccagaaaaca tgtaccttca aggaactggt atatgaaaca      180
gtgagagtgc ccggctgtgc tcaccatgca gattccttgt atacataccc agtggccacc      240
cagtgtcact gtggcaagtg tgacagcgac agcactgatt gtactgtgcg aggcctgggg      300
cccagctact gctcctttgg tgaaatgaaa gaa                                   333
```

<210> SEQ ID NO 19
<211> LENGTH: 276
<212> TYPE: DNA
<213> ORGANISM: Artificial Sequence
<220> FEATURE:
<223> OTHER INFORMATION: Description of Artificial Sequence: Modified
      to facilitate cloning.

<400> SEQUENCE: 19

```
gctcctgatg tgcaggattg cccagaatgc acgctacagg aaaacccatt cttctcccag        60
ccgggtgccc caatacttca gtgcatgggc tgctgcttct caagagcata tcccactcca       120
ctaaggtcca agaagacgat gttggtccaa aagaacgtca cctcagagtc cacttgctgt       180
gtagctaaat catataacag ggtcacagta atggggggtt tcaaagtgga gaaccacacg       240
gcgtgccact gcagtacttg ttattatcac aaatct                                 276

<210> SEQ ID NO 20
<211> LENGTH: 324
<212> TYPE: DNA
<213> ORGANISM: Artificial Sequence
<220> FEATURE:
<223> OTHER INFORMATION: Description of Artificial Sequence: Modified
      to facilitate cloning.

<400> SEQUENCE: 20
aacagctgtg agctcaccaa catcaccatt gcaatagaga aagaagaatg tcgtttctgc        60
atatcgatca acaccacttg gtgtgctggc tactgctaca ccagggatct ggtgtataag       120
gacccggccc gtcccaaaat ccagaaaaca tgtaccttca aggaactggt atatgaaaca       180
gtacgcgtgc ccggctgtgc tcaccatgca gattccttgt atacataccc agtggccacc       240
cagtgtcact gtggcaagtg tgacagcgac agcactgatt gtactgtgcg aggcctgggg       300
cccagctact gctcctttgg tgaa                                              324
```